United States Patent
Lambrecht et al.

(10) Patent No.: US 10,492,825 B2
(45) Date of Patent: Dec. 3, 2019

(54) SEALING MULTIPLE SURGICAL INSTRUMENTS

(71) Applicant: INTUITIVE SURGICAL OPERATIONS, INC., Sunnyvale, CA (US)

(72) Inventors: Bram Gilbert Antoon Lambrecht, Sunnyvale, CA (US); William J. Park, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 1306 days.

(21) Appl. No.: 14/211,603

(22) Filed: Mar. 14, 2014

(65) Prior Publication Data

US 2014/0276464 A1    Sep. 18, 2014

Related U.S. Application Data

(60) Provisional application No. 61/800,632, filed on Mar. 15, 2013.

(51) Int. Cl.
*A61B 17/34* (2006.01)
*A61B 90/00* (2016.01)
*A61B 34/30* (2016.01)

(52) U.S. Cl.
CPC ...... *A61B 17/3421* (2013.01); *A61B 17/3462* (2013.01); *A61B 17/3498* (2013.01);
(Continued)

(58) Field of Classification Search
CPC ............ A61B 17/3421; A61B 17/3462; A61B 17/3498; A61B 2017/3464;
(Continued)

(56) References Cited

U.S. PATENT DOCUMENTS

| | | |
|---|---|---|
| 4,436,519 A | 3/1984 | O'Neill |
| 5,030,206 A | 7/1991 | Lander |

(Continued)

FOREIGN PATENT DOCUMENTS

| | | |
|---|---|---|
| EP | 2467074 A2 | 6/2012 |
| JP | H07508899 A | 10/1995 |

(Continued)

OTHER PUBLICATIONS

Final Office Action dated Apr. 28, 2016 for U.S. Appl. No. 14/212,188, filed Mar. 14, 2014, 10 pages.
(Continued)

*Primary Examiner* — Imani N Hayman
*Assistant Examiner* — Tiffany Legette
(74) *Attorney, Agent, or Firm* — Schwegman Lundberg & Woessner, P.A.

(57) ABSTRACT

A cannula seal is presented. The cannula seal includes a cross-slit seal that can include a side wall that includes folded sidewalls; slits that are formed by the folded sidewalls when the cross-slit seal is in a closed position; and a concave end surface at the slits. The cross-slit seal can include energizing ribs formed to close the seal. The instrument guide includes a pyramidal shaped seal that seals against doors when no instrument is inserted and seals against an instrument when the instrument is inserted.

23 Claims, 33 Drawing Sheets

(52) U.S. Cl.
CPC ............ *A61B 34/30* (2016.02); *A61B 90/361* (2016.02); *A61B 2017/3445* (2013.01); *A61B 2017/3464* (2013.01); *A61B 2017/3466* (2013.01); *Y10T 137/7885* (2015.04)

(58) Field of Classification Search
CPC .... A61B 2017/3466; A61B 2017/3445; A61B 34/30; A61M 39/26; F16K 15/14; F16K 15/147; A47G 19/2272; A61F 21/2412
USPC ...................... 604/265, 256, 167.04; 137/849
See application file for complete search history.

(56) References Cited

U.S. PATENT DOCUMENTS

| | | | |
|---|---|---|---|
| 5,141,498 A | 8/1992 | Christian | |
| 5,232,450 A | 8/1993 | Green et al. | |
| 5,269,763 A | 12/1993 | Boehmer et al. | |
| 5,407,433 A | 4/1995 | Loomas | |
| 5,411,483 A | 5/1995 | Loomas et al. | |
| 5,443,452 A * | 8/1995 | Hart ................. | A61B 17/3498 137/849 |
| 5,545,142 A | 8/1996 | Stephens et al. | |
| 5,792,113 A | 8/1998 | Kramer et al. | |
| 5,830,196 A | 11/1998 | Hicks | |
| 6,018,094 A | 1/2000 | Fox | |
| 6,066,117 A | 5/2000 | Fox et al. | |
| 6,162,196 A * | 12/2000 | Hart ................. | A61B 17/3462 604/167.02 |
| 6,217,555 B1 | 4/2001 | Hart et al. | |
| 6,228,061 B1 | 5/2001 | Flatland et al. | |
| 6,458,077 B1 | 10/2002 | Boebel et al. | |
| 6,595,946 B1 | 7/2003 | Pasqualucci | |
| 8,034,032 B2 | 10/2011 | Voegele et al. | |
| 8,784,435 B2 | 7/2014 | Cooper et al. | |
| 9,888,941 B2 | 2/2018 | Lambrecht et al. | |
| 10,070,887 B2 | 9/2018 | Lambrecht et al. | |
| 2004/0111060 A1 | 6/2004 | Racenet et al. | |
| 2004/0236347 A1 | 11/2004 | Karasawa | |
| 2005/0070851 A1 | 3/2005 | Thompson et al. | |
| 2005/0090779 A1 | 4/2005 | Osypka | |
| 2005/0267487 A1 * | 12/2005 | Christensen ....... | A61B 17/3415 606/108 |
| 2007/0088277 A1 | 4/2007 | McGinley et al. | |
| 2009/0005799 A1 * | 1/2009 | Franer ............... | A61B 17/3462 606/185 |
| 2009/0149813 A1 | 6/2009 | Franer et al. | |
| 2009/0192466 A1 | 7/2009 | Sniffin | |
| 2010/0004599 A1 | 1/2010 | Zhou et al. | |
| 2010/0081995 A1 | 4/2010 | Widenhouse et al. | |
| 2010/0240960 A1 | 9/2010 | Richard | |
| 2010/0268164 A1 | 10/2010 | Chung | |
| 2011/0060183 A1 | 3/2011 | Castro et al. | |
| 2011/0201883 A1 | 8/2011 | Cooper et al. | |
| 2011/0282358 A1 | 11/2011 | Gomez et al. | |
| 2011/0295077 A1 | 12/2011 | Stefanchik et al. | |
| 2012/0283518 A1* | 11/2012 | Hart .................. | A61B 17/3462 600/207 |
| 2013/0178885 A1 | 7/2013 | Lee | |
| 2014/0275791 A1 | 9/2014 | Lambrecht et al. | |
| 2014/0276465 A1 | 9/2014 | Lambrecht et al. | |
| 2014/0276946 A1 | 9/2014 | Lambrecht et al. | |
| 2014/0276947 A1 | 9/2014 | Lambrecht et al. | |
| 2018/0221053 A1 | 8/2018 | Lambrecht et al. | |

FOREIGN PATENT DOCUMENTS

| | | |
|---|---|---|
| JP | 2007501660 A | 2/2007 |
| JP | 2012075874 A | 4/2012 |
| JP | 2012515022 A | 7/2012 |
| WO | WO-2014144771 A1 | 9/2014 |

OTHER PUBLICATIONS

Final Office Action dated Apr. 29, 2016 for U.S. Appl. No. 14/211,907, filed Mar. 14, 2014, 9 pages.
Non-Final Office Action dated Oct. 6, 2016 for U.S. Appl. No. 14/212,188, filed Mar. 14, 2014, 7 pages.
Non-Final Office Action dated Oct. 27, 2015 for U.S. Appl. No. 14/211,907, filed Mar. 14, 2014, 7 pages.
Response filed Jan. 5, 2016 for Non-Final Office Action dated Oct. 6, 2016 for U.S. Appl. No. 14/212,188, filed Mar. 14, 2014, 16 pages.
Response filed Jan. 27, 2016 for Non-Final Office Action dated Oct. 27, 2015 for U.S. Appl. No. 14/211,907, filed Mar. 14, 2014, 14 pages.
Notice of Allowance dated Jul. 28, 2016 for U.S. Appl. No. 14/211,907, filed Mar. 14, 2014, 10 pages.
Response filed Jun. 28, 2016 for Final Office Action dated Apr. 28, 2016 for U.S. Appl. No. 14/212,188, filed Mar. 14, 2014, 17 pages.
Response filed Jun. 29, 2016 for Final Office Action dated Apr. 29, 2016 for U.S. Appl. No. 14/211,907, filed Mar. 14, 2014, 19 pages.
Restriction Requirement dated Jul. 29, 2016 for U.S. Appl. No. 14/211,713, filed Mar. 14, 2014, 6 pages.
International Search Report and Written Opinion for Application No. PCT/US2014/029321, dated Jul. 25, 2014, 15 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. 14765569.0, dated Jan. 18, 2017, 9 pages.
Partial Supplementary European Search Report for Application No. 14765569.0, dated Oct. 4, 2016, 7 pages.
Extended European Search Report for Application No. 19165014.2 dated Jun. 18, 2019, 7 pages.

* cited by examiner

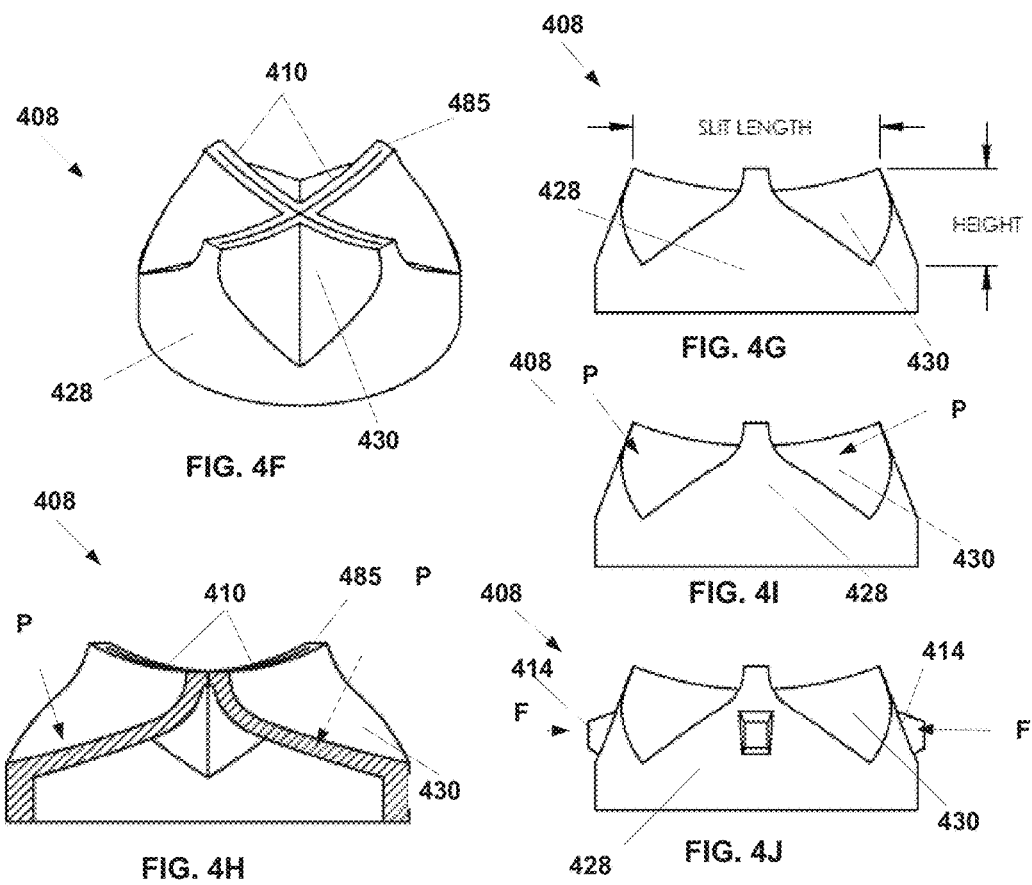

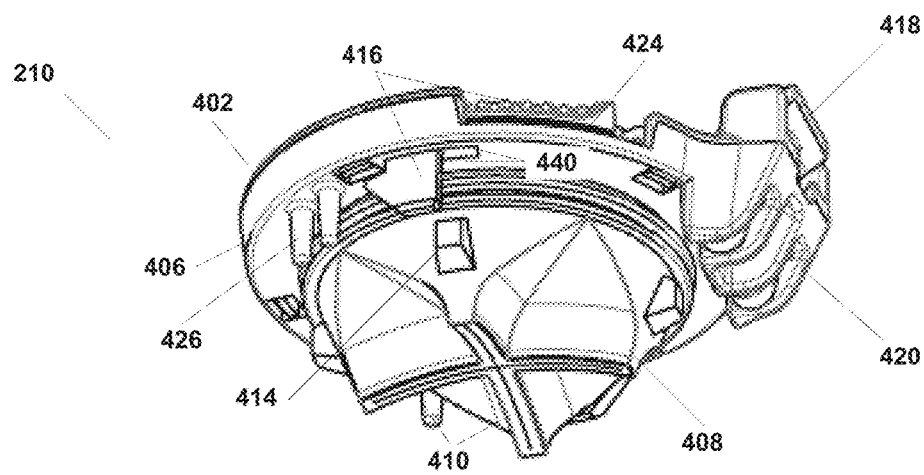
FIG. 4P
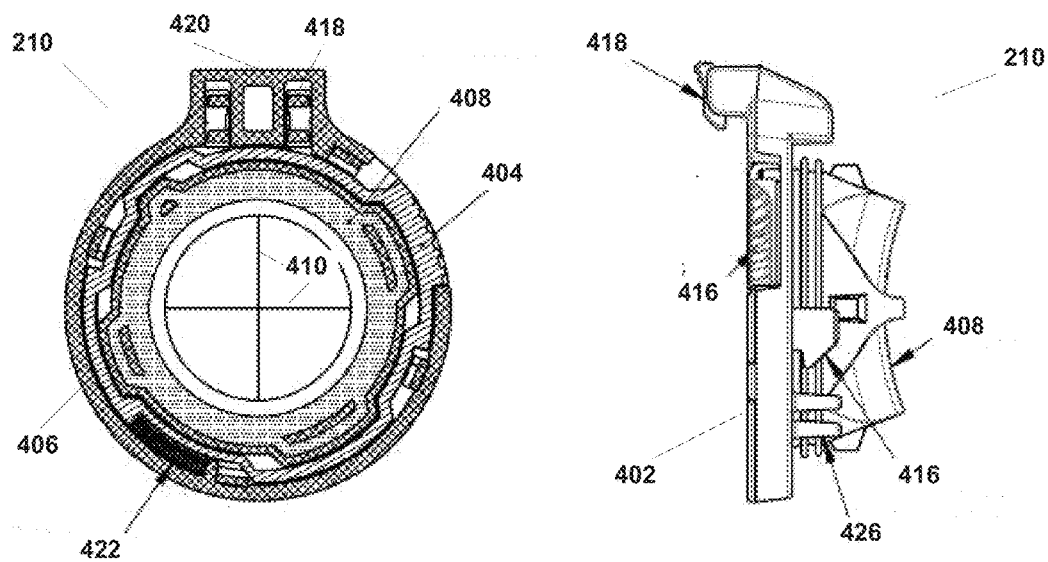
FIG. 4Q
FIG. 4R

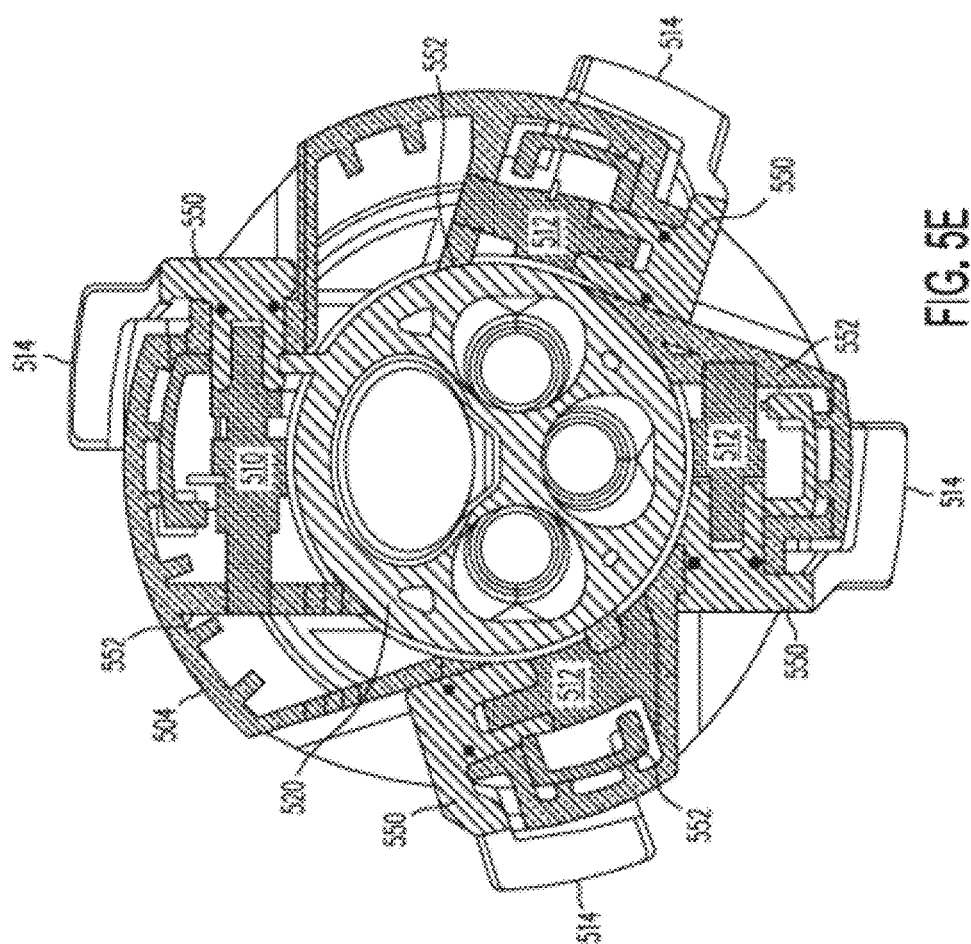

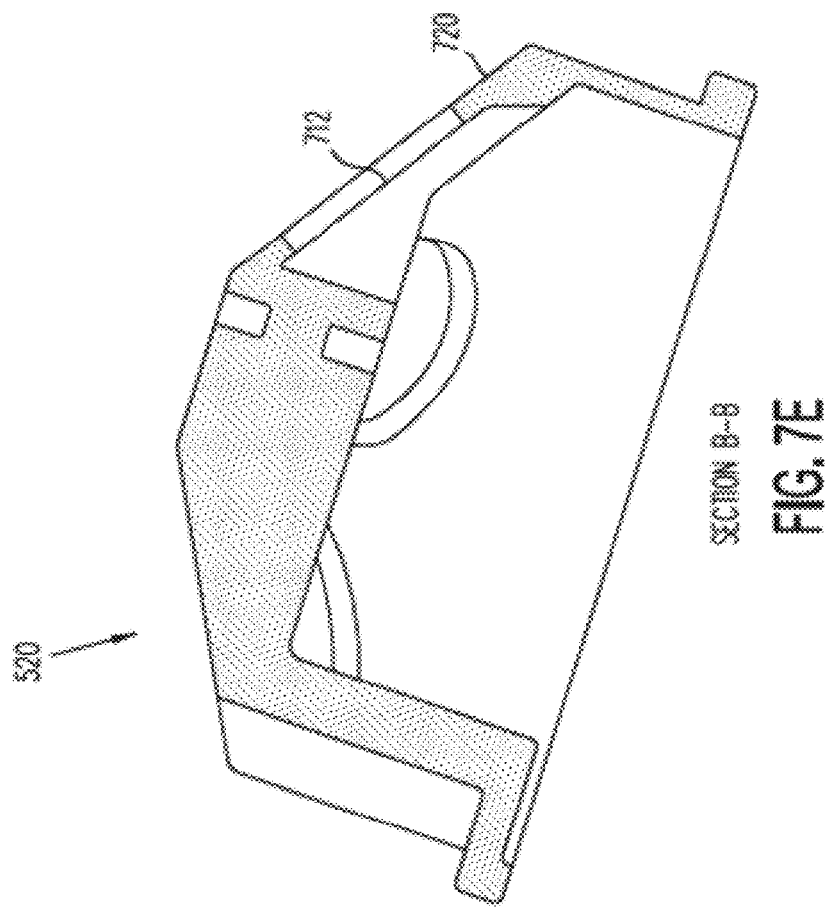
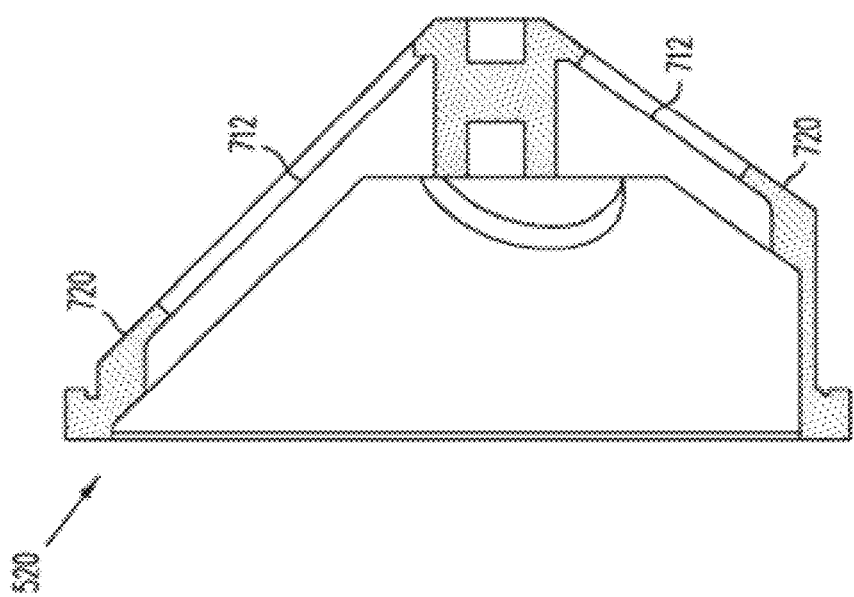

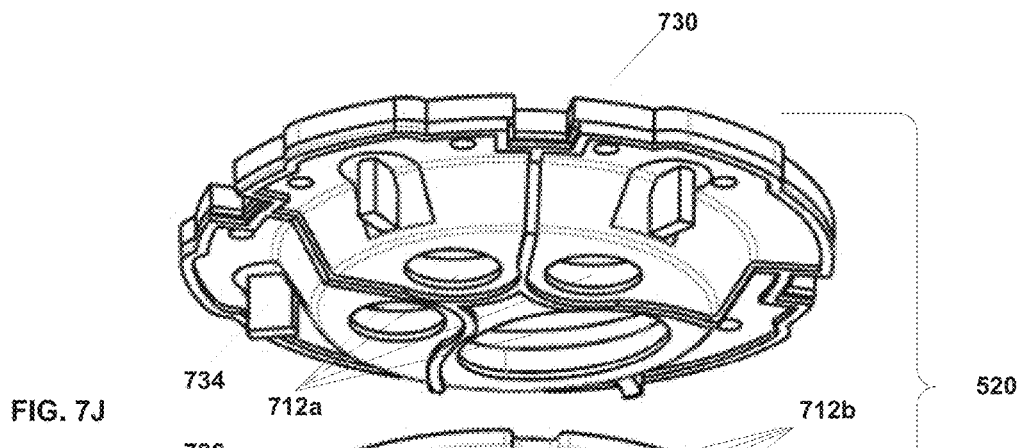
FIG. 7J
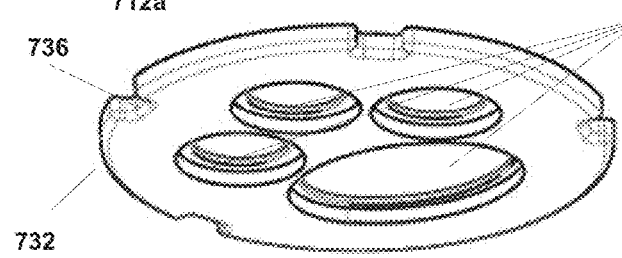
FIG. 7K
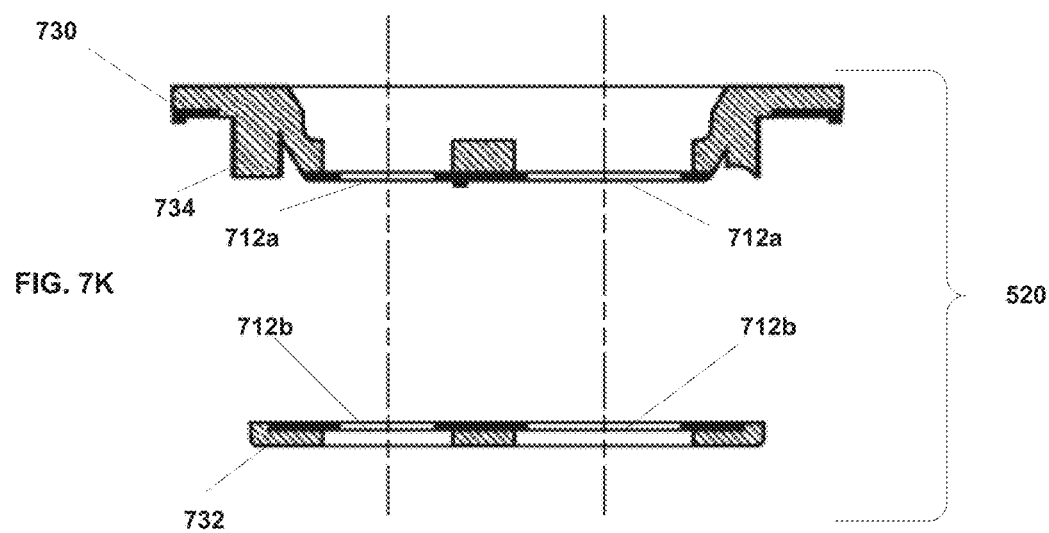

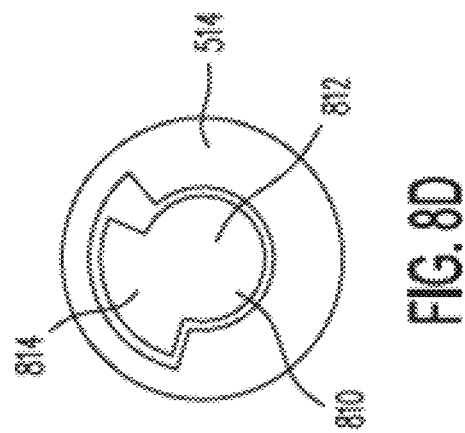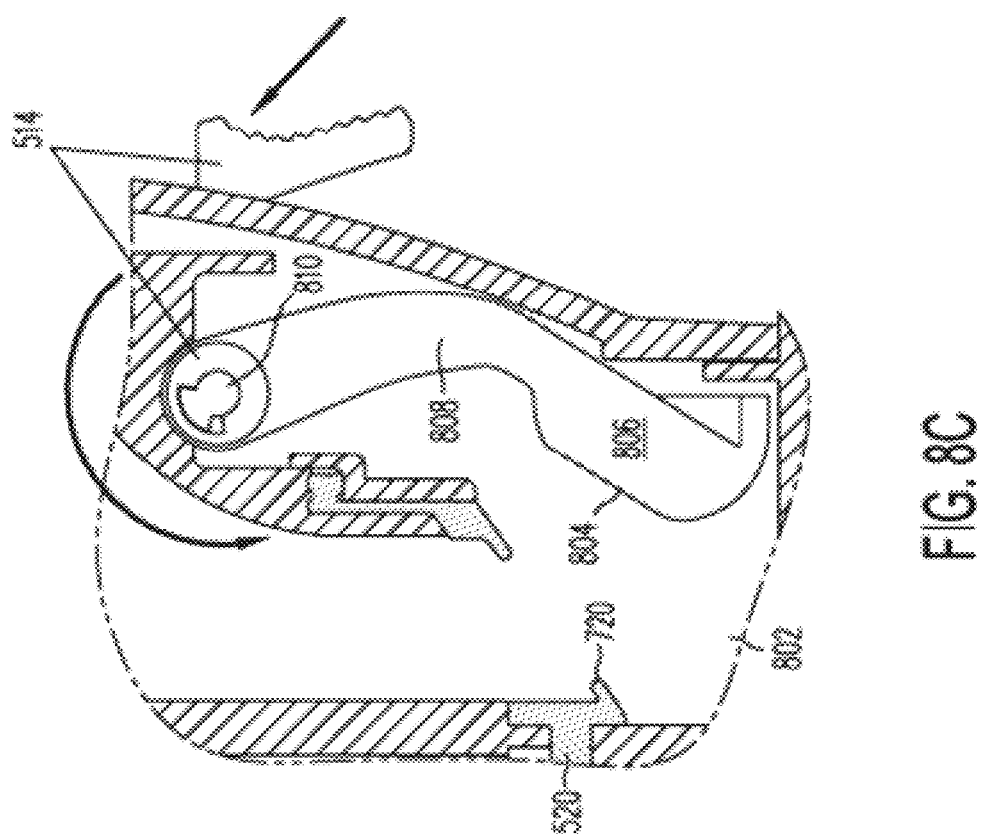

SEALING MULTIPLE SURGICAL INSTRUMENTS

RELATED APPLICATIONS

This disclosure claims priority to U.S. Provisional Patent Application Ser. No. 61/800,632, filed on Mar. 15, 2013, which is herein incorporated by reference in its entirety.

BACKGROUND

Technical Field

Embodiments of the present invention are related to teleoperated robotic surgery and, in particular, to sealing multiple surgical instruments in a single cannula.

Discussion of Related Art

Minimally invasive surgery (MIS) (e.g., endoscopy, laparoscopy, thoracoscopy, cystoscopy, and the like) allows a patient to be operated upon through small incisions by using a camera and one or more elongated surgical instruments introduced to an internal surgical site. The surgical site often comprises a body cavity, such as the patient's abdomen. The body cavity may optionally be distended using a clear fluid such as an insufflation gas, typically $CO_2$. In traditional minimally invasive surgery, the surgeon manipulates the tissues by using hand-actuated end effectors of the elongated surgical instruments while viewing the surgical site on a video monitor.

One or more cannulas may be passed through small (generally 7 cm or less) incisions or a natural body orifice to provide entry ports for the minimally invasive (e.g., endoscopic, laparoscopic, and the like) surgical instruments, including a camera instrument (e.g., endoscope, laparoscope, and the like). A surgeon is able to perform surgery by manipulating the surgical instruments from outside the body while viewing the instrument end effectors at the internal surgical site with images provided by the camera instrument.

It is typical to provide several cannulas for a minimally invasive surgical procedure. Generally, each cannula will provide access to the surgical site for a single surgical or camera instrument. For example, four cannulas may be provided with one cannula being used to introduce a camera instrument and the remaining three cannulas being used to introduce surgical instruments. The use of two or more separate entry points to access a surgical site may be considered "multi-port" minimally invasive surgery. While the small incisions necessary for placing a cannula are less traumatic than the incision necessary for open surgery, each incision still represents a trauma to the patient.

In an effort to reduce the trauma of minimally invasive surgery even further, techniques are being developed to allow minimally invasive surgery using only a single access port into the body, such as a single incision or single natural body orifice. This access may be accomplished by using a somewhat larger cannula that can accommodate all of the instruments required for the surgery. Minimally invasive surgery performed through a single incision or natural orifice may be referred to as single port access (SPA) surgery. The single cannula that provides the single port may be introduced through a body orifice or through an incision.

If multiple surgical instruments and/or camera instruments are to be introduced to a surgical site through a single cannula, it can become difficult to manage the instruments within the cannula. It is desirable to use as small a cannula as possible, consistent with the size of the instruments to be passed through the cannula. This may make it difficult to introduce the necessary instruments and to maintain the necessary mobility of the instruments as well as to prevent the insufflation gas from escaping via the access port as various instruments are inserted and removed from the cannula, as well as during instrument use during surgery.

Therefore, there is a need to develop systems for better and more effective access to the surgical area.

SUMMARY

In accordance with aspects of the present invention, a cannula seal is provided. A cannula seal can be a cross-slit seal. The cross-slit seal can include a side wall that includes folded sidewalls; slits that are formed by the folded sidewalls when the cross-slit seal is in a closed position; and a concave end surface at the slits.

In some embodiments, a cross-slit seal can include a side wall that includes folded sidewalls; slits that are formed by the folded sidewalls when the cross-slit seal is in a closed position; and ribs formed in the side wall that engage an inside wall of a cannula.

These and other embodiments are further discussed below with respect to the following figures.

BRIEF DESCRIPTION OF THE DRAWINGS

FIGS. 4F-4J illustrate some embodiments of a cross-slit seal that can be utilized with many cannulas.

FIGS. 4P-4R illustrate embodiments of an assembled cannula cap and seal as illustrated in FIG. 4D.

FIGS. 5B-5E illustrate an instrument guide according to some embodiments of the present invention.

FIGS. 7C, 7D, and 7E illustrate an instrument seal as shown in FIG. 7A and certain cross sections of that instrument seal.

FIGS. 7J and 7K illustrate another embodiment of an instrument seal.

FIGS. 8A-8D illustrate a door mechanism according to some embodiments of the present invention.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art will realize other elements that, although not specifically described here, are within the scope and the spirit of this disclosure. In addition, to avoid unnecessary repetition in the following description, one or more features shown and described in association with one embodiment may be incorporated into other embodiments unless specifically described otherwise, unless the one or more features would make an embodiment non-functional, or unless two or more of the features provide conflicting functions.

Further, this description's terminology is not intended to limit the scope of the invention. For example, spatially relative terms—such as "beneath", "below", "lower", "above", "upper", "proximal", "distal", "horizontal", "vertical" and the like—may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations), and the spatially relative descriptors used herein interpreted accordingly. Likewise, descriptions of movement along and around various axes include various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Figure 1:
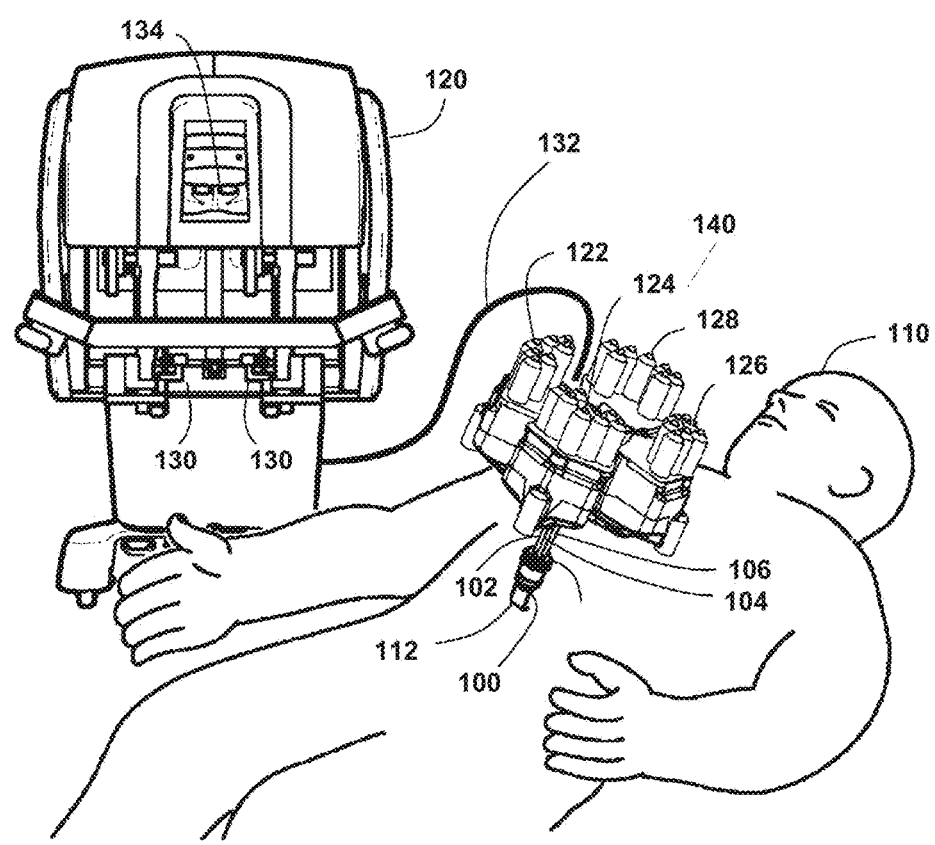
FIG. 1 illustrates components of a single-port teleoperated robotic surgical system.

FIG. 1 shows a pictorial view of a minimally invasive surgery on a patient 110 using single access port 100 for teleorobotic surgical instruments 102, 104, 106. Single access port 100 is inserted through a single incision 112. Typically three or four surgical instruments (instruments 102, 104, and 106 are illustrated), including a camera instrument, are introduced through single access port 100. In addition, there will generally be provisions for introducing an insufflation gas, such as carbon dioxide ($CO_2$), at or near single access port 100. It will be appreciated that single port surgery utilizes a substantial amount of equipment located in a small amount of space.

The teleorobotic surgical instruments 102, 104, and 106, which may include a camera instrument that may provide images of the surgical site and other instruments at the surgical site, are each coupled to a corresponding actuator, such as one of actuators 122, 124, 126, and 128. Actuators 122, 124, 126, and 128 are servo actuators that allow a surgeon to manipulate the surgical instruments using a computer-mediated control station 120 and are mounted on teleoperated robot 140. These manipulations may include functions such as changing the position and orientation of the surgical instrument's end effector (to include a camera) and operating the end effector (such as closing jaws to effect grasping, cutting, etc.). Such actuator control of surgical instruments may be referred to by various terms, such as robotic surgery or telerobotics. Actuators 122, 124, 126, and 128 of teleoperated robot 140 may be supported on a separate structural robotic arm that, once positioned, can be fixed relative to patient 110. In various implementations the supporting robot arm may be manually positioned, may be positioned by the surgeon, or may be automatically positioned by the system as the surgeon moves one or more of the surgical instruments. U.S. patent application Ser. No. 12/855,452 (filed Aug. 12, 2010; published as US 2011/0282358 A1), incorporated herein by reference, shows additional illustrative aspects of a single port robotic surgical system.

A control system couples a computer-mediated control station 120 to the robotic actuators 122, 124, 126, and 128. Here "computer" broadly encompasses a data processing unit that incorporates a memory and an additive or logical function, such as an arithmetic logic unit, that is programmable to perform arithmetic or logical operations. The control system may coordinate movement of the input devices with the movement of their associated surgical instruments so that the images of the surgical instruments 102, 104, 106, as displayed to the surgeon, appear at least substantially connected to the input devices in the hands of the surgeon. Further levels of connection will also often be provided to enhance the surgeon's dexterity and ease of use of the surgical instruments 102, 104, and 106.

The computer-mediated control station 120 may provide hand operated master controllers 130 that allow manipulation of the teleorobotic slave surgical instruments 102, 104, 106 by transmitting signals, such as electrical or optical control signals provided by cables 132, to the actuators 122, 124, 126, and 128 that control the actions of the coupled surgical instruments 102, 104, and 106. Typically one of the surgical instruments, surgical instrument 102 for example, will be a camera instrument that is manipulated to place the remaining surgical instruments and the objects being manipulated within a field of view of the camera. The camera instrument transmits signals to the control station 120 so that an image captured by the camera of the instruments and objects within the field of view can be displayed on a visual display 134 that is viewed by the surgeon as the coupled surgical instruments 104, 106 are manipulated. The hand-operated controllers 130 and the visual display 134 may be arranged to provide an intuitive control of the surgical instruments 104, 106, in which the instruments move in a manner similar to the operator's hand movements with the controllers.

FIGS. 2A, 2B, 2C, and 2D illustrate general aspects of an access port 100 that can be inserted through incision 112 according to some embodiments of the present invention.

Access port 100 provides the single port access as shown in FIG. 1. Access port 100 includes a cannula 202 and an instrument guide 204 that is inserted into cannula 202. Cannula 202 can include a latch feature 212 (either an object held by a latch or a latch itself) so that access port 100 can be coupled to teleoperated robot 140 or other holder.

Figure 2A:
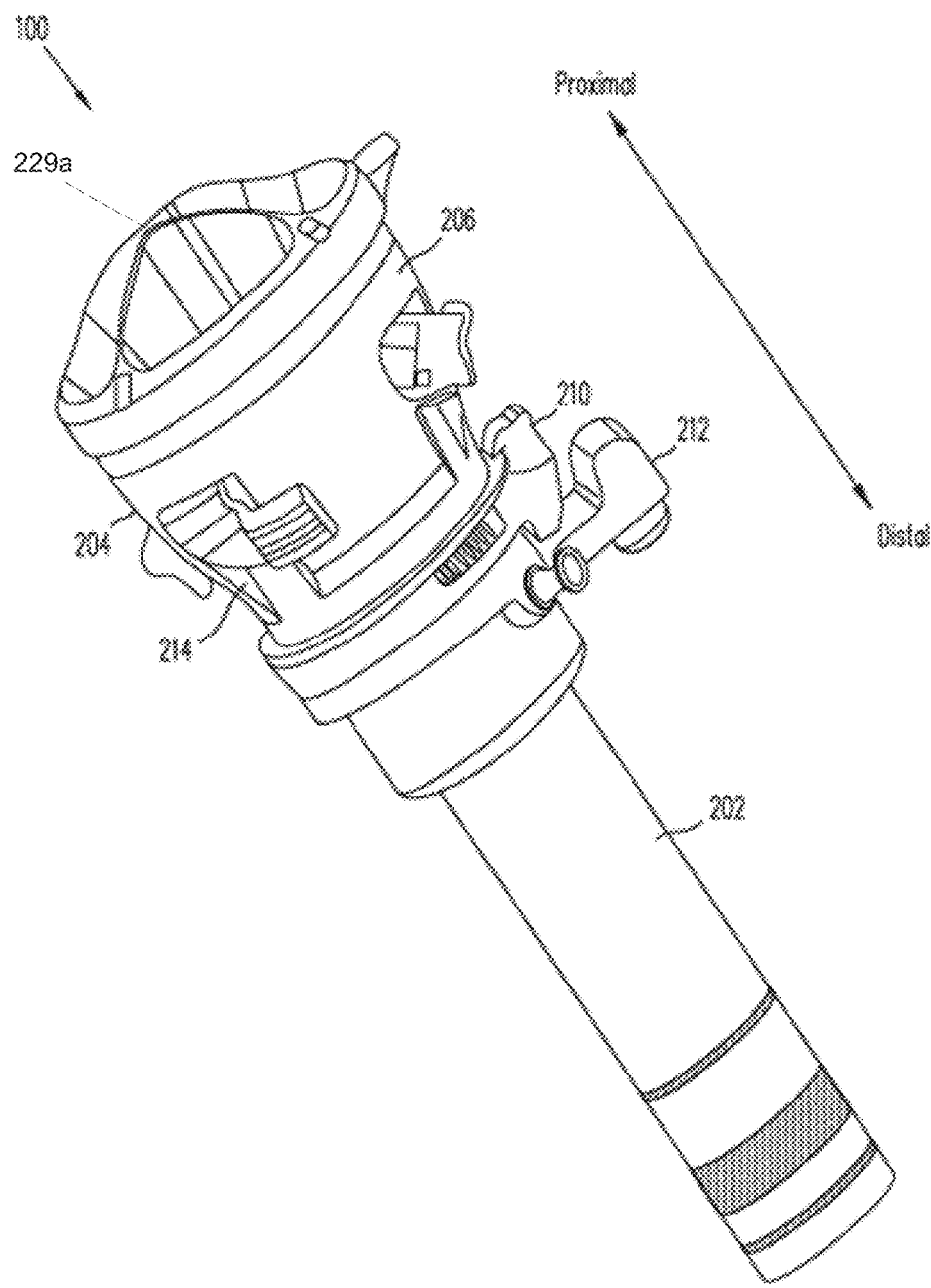
FIGS. 2A, 2B, 2C, and 2D illustrate an access port according to some embodiments of the present invention.
Figure 2B:
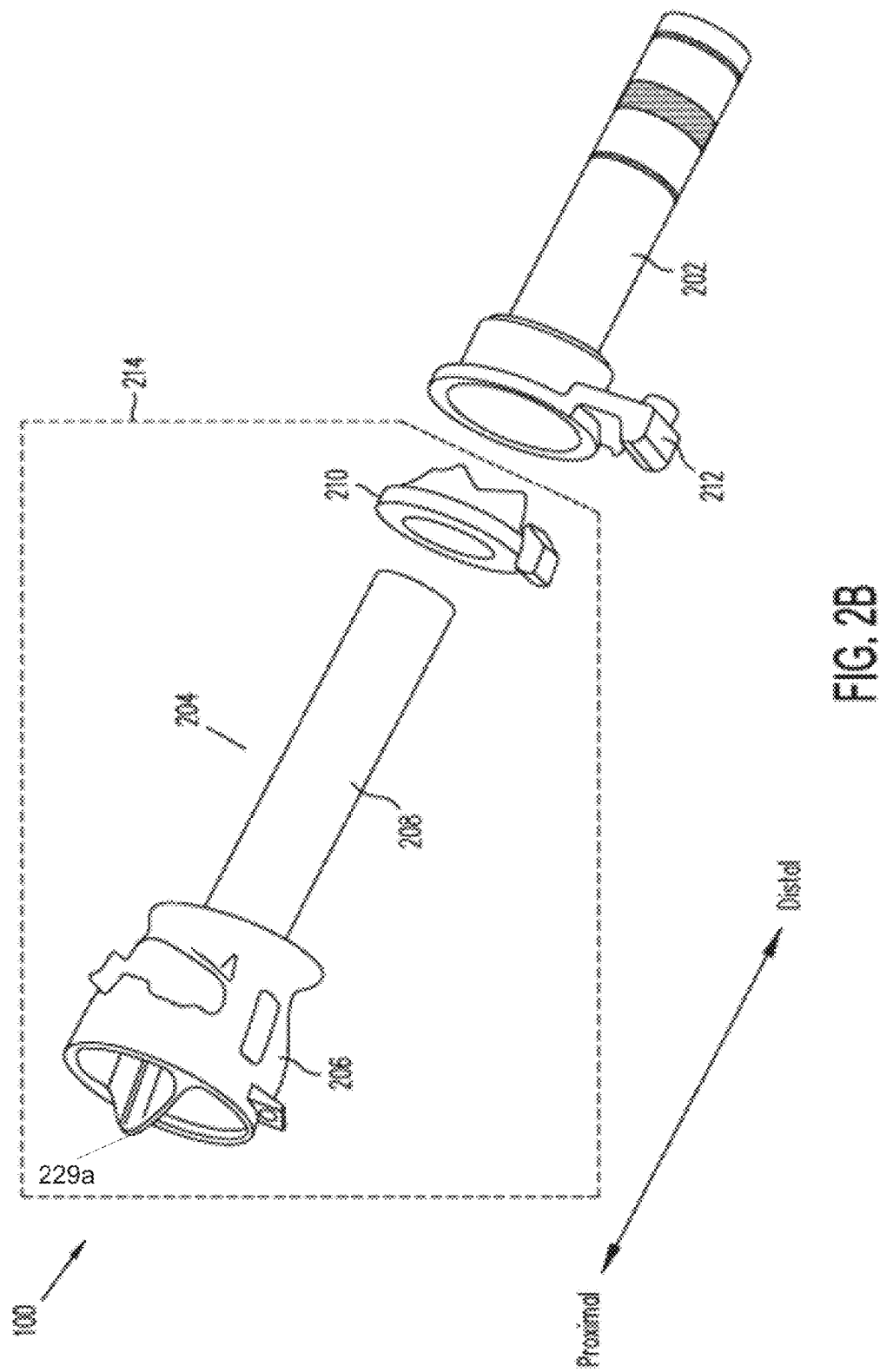

Instrument guide 204 guides multiple instruments through cannula 202 to facilitate multiple instrument single port access. As illustrated in FIG. 2B, instrument guide 204 includes a channel portion 208 and a funnel portion 206. Instrument guide 204 may be coupled to cannula 202 in various ways. For example, as further illustrated in FIG. 2B, a cannula cap 210 can be snapped onto cannula 202, and channel portion 208 is inserted through cannula cap 210 so that funnel portion 206 snaps onto cannula cap 210. Cannula cap 210 may be omitted in some embodiments, and instrument guide 204 is mated directly with cannula 202.

Figure 2C:
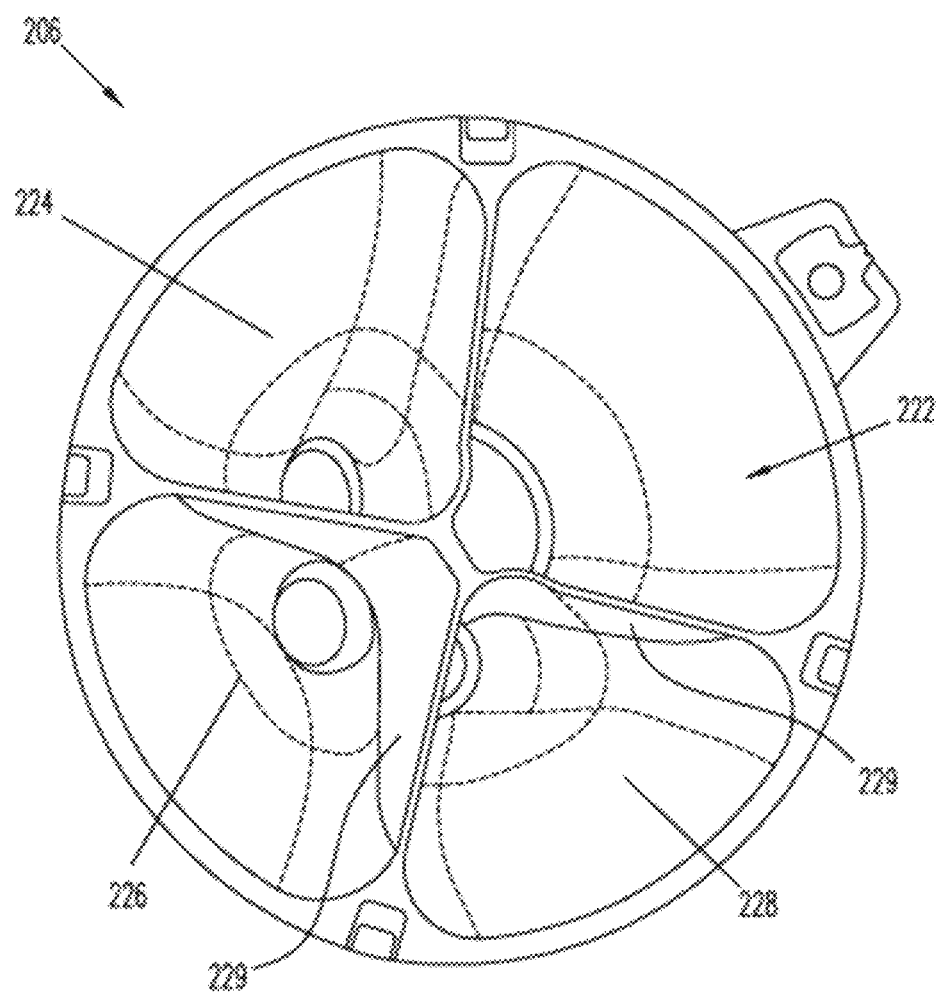
Figure 2D:
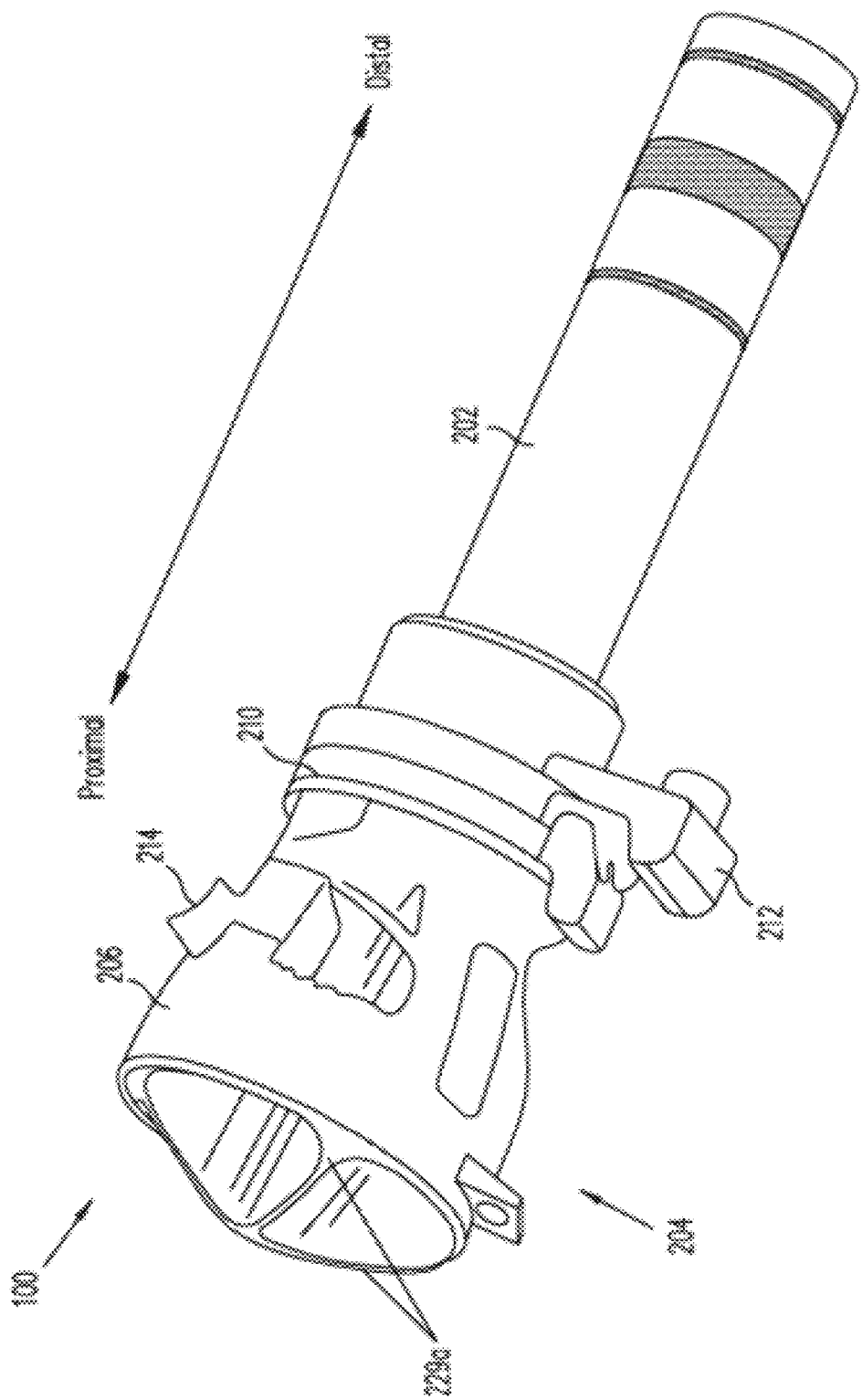

Funnel portion 206 guides instruments into channel portion 208. Channel portion 208 can include four illustrative instrument channels (which may be termed "lumens") through which instruments are guided from the manipulator towards the surgical site. Accordingly, funnel portion 206 is divided into four funnel guides, each funnel guide corresponding to an associated instrument channel. FIG. 2C is a top view into funnel portion 206, and it illustrates funnel guides 222, 224, 226, and 228 that direct instruments into corresponding channels of channel portion 208. It can be seen that funnel guides 222, 224, 226, and 228 are separated from one another by walls 229, and as shown in FIGS. 2A, 2B, and 2D the top edges 229a of these separating walls extend proximally from instrument guide 204 (they are shown as convex). This extension helps to guide an instrument into the proper one of funnel guides 222, 224, 226, or 228 during instrument insertion and mounting to the teloperated robot 140. The instrument channels may be sized and shaped to accommodate various different instruments, and so FIG. 2C also shows that one funnel guide, funnel guide 222, is larger with a different cross-sectional shape than the other funnel guides, funnel guides 224, 226, and 228, to receive a relatively larger instrument such as, for example, camera surgical instrument 102.

Channel portion 208 is configured to fit closely within cannula 202. Each of the channels of channel portion 208 is configured to support a single one of the surgical instruments at a defined position within cannula 202. The surgical instruments are inserted into the access port 100 through funnel portion 206 so that they are directed into the channels at a proximal end of the instrument guide 204. The surgical instruments are supported by the channels until they emerge from a distal end of the instrument guide 204. Instrument guide 204 may be formed from an electrically non-conductive material to aid in electrically isolating the instruments, which may carry an electrical charge used for electrosurgical applications (e.g., cauterization).

Cap 210 provides a general insufflation seal for cannula 202, as discussed in detail below. In alternative embodiments, such an insufflation seal may be removably or permanently mounted in cannula 202, and items to be inserted into and held within cannula 202 are coupled directly to cannula 202 instead of using a cap. The cap provides an easy way of quickly mounting and removing a seal to the cannula, which can have an inner diameter on the order of 25 mm—significantly larger than current multi-port cannula inner diameters, which range from about 5 mm to 13 mm—and provides mounting features for the items inserted within the cannula.

As shown in FIG. 2B, a kit 214 can be formed of cap 210 and instrument guide 204. In some embodiments, cannula 202 can be reusable (e.g., after cleaning and sterilization). The components of kit 214 can be sold as a sterile kit, e.g., a gamma sterilized kit, so that a new instrument guide 204 and a new cap 210 may be used for each surgical procedure.

The cannula cap 210 snaps onto the cannula 202, and the instrument guide 204 snaps into cap 210. Alternatively, as discussed below, an obturator 302 (FIG. 3A) or other device to be inserted into and held within cannula 202 can snap onto cap 210 in a similar way. The individual pieces that make up cannula cap 210 or instrument guide 204 can be fully assembled during manufacturing, typically not by the user. The assembly method may include the use of permanent snaps, gluing, fasteners, heat staking, ultrasonic welding, or any other attachment method. Details of the cap design and instrument guide design are discussed in more detail below.

Figure 3A:
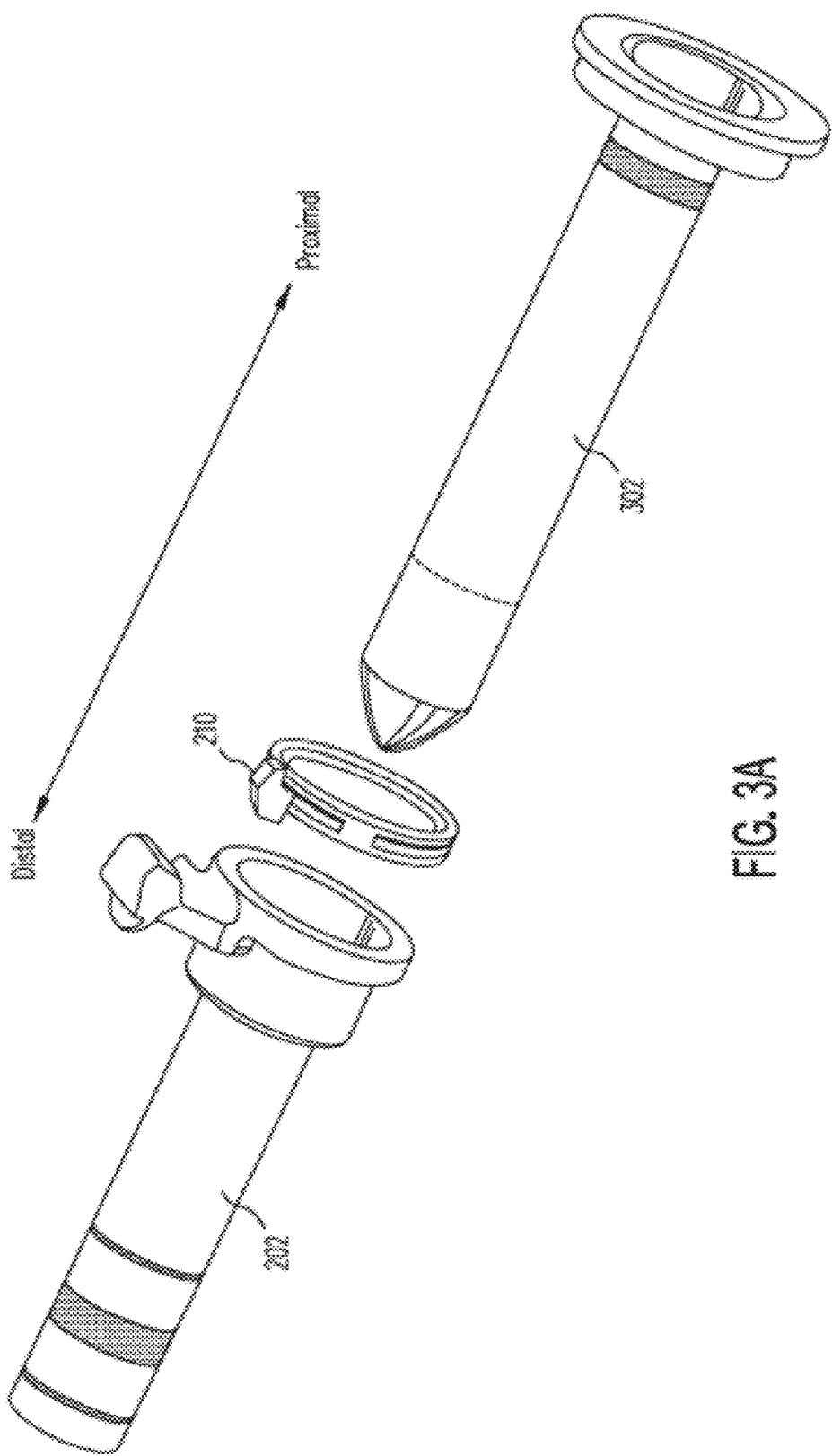
FIGS. 3A and 3B illustrate utilization of an obturator according to some embodiments of the present invention.
Figure 3B:
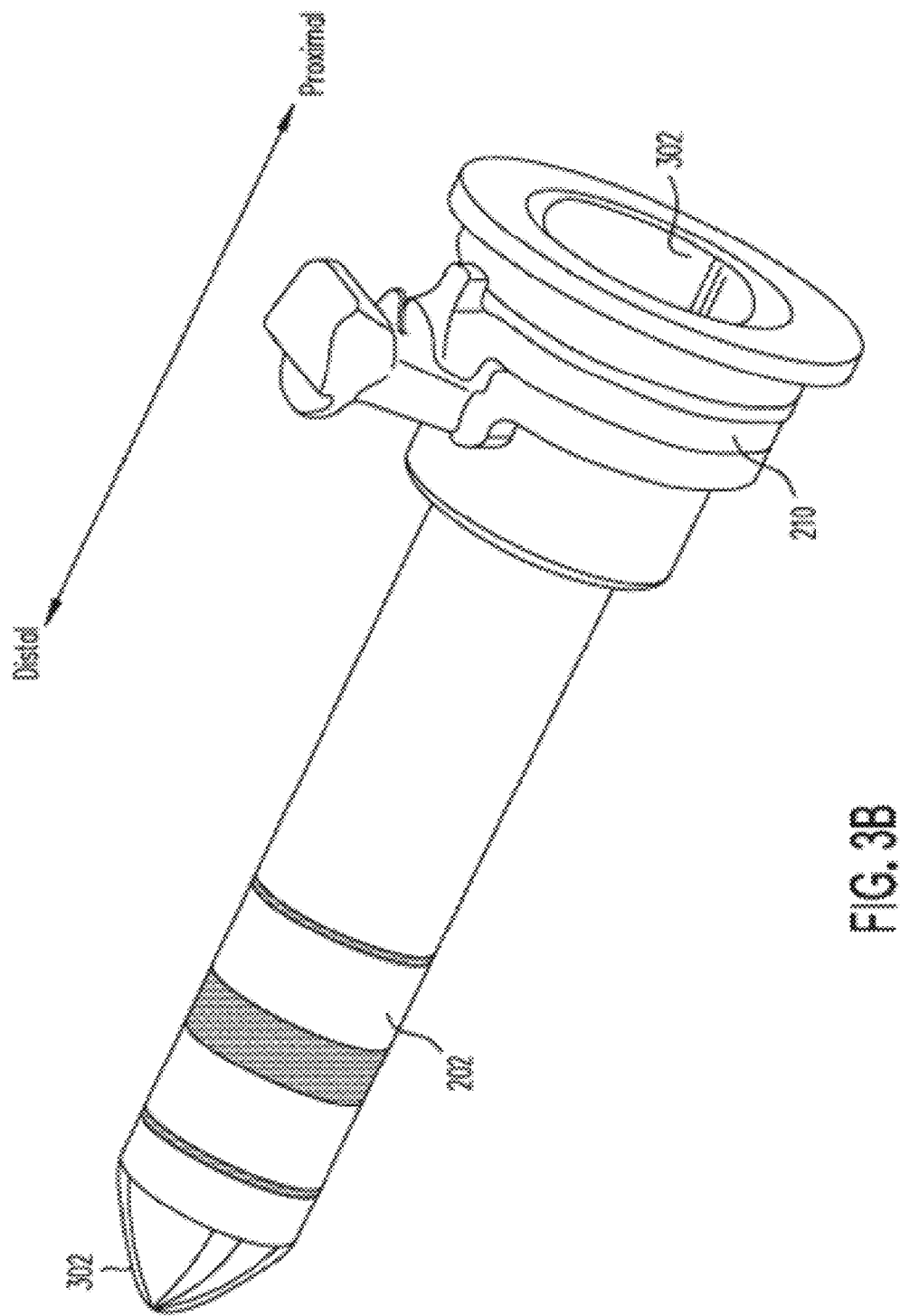

FIGS. 3A and 3B illustrate an example in which an obturator 302 is inserted through cap 210. FIG. 3A illustrates cannula 202 with cap 210 and obturator 302. FIG. 3B illustrates cannula 202, cap 210, and obturator 302 assembled. Once cannula 202 has been established in incision 112, obturator 302 can be removed and replaced with instrument guide 204, as is illustrated in FIGS. 2A and 2D. As explained below, a seal in cap 210 preserves insufflation pressure at the surgical site by preventing insufflation gas from escaping through cannula 202. Obturator 302 may be made to be usable for many surgical procedures, or it may be made for use during a single surgical procedure (i.e., "disposable"). If made for use during a single procedure, a sterilized obturator 302 (e.g., gamma sterilized) may be included in sterile kit 214.

As shown in FIGS. 2A through 2D and in FIGS. 3A and 3B, cap 210 can fasten into cannula 202 and be fixed in place. Further, instrument guide 204 or obturator 302 fasten into cap 210. A release mechanism, either on cap 210 or on the inserted object (instrument guide 204 or obturator 302) can allow for the removal of instrument guide 204 or obturator 302 from the cannula 202 and cap 210 combination. In some embodiments, cap 210 allows instrument guide 204 to rotate inside cannula 202. In some embodiments, single port 100 may not include a cap 210.

Cannula Cap and Seal

Figure 4A:
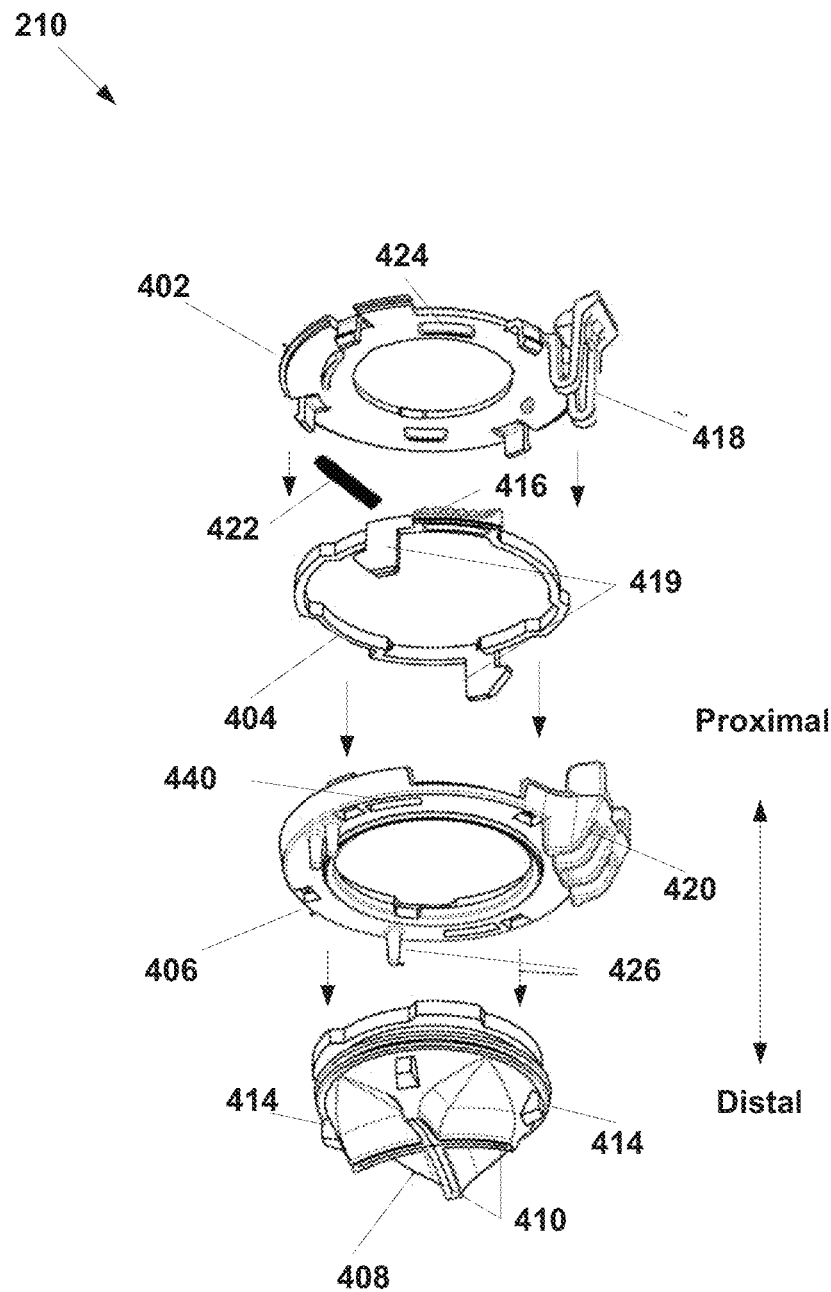
FIG. 4A illustrates a cannula cap according to some embodiments of the present invention.

A cap 210 is illustrated, for example, in FIGS. 2A and 2B. As shown, cap 210 can be releasably attached to cannula 202 and releasably attached to instrument guide 204. The cap 210 also positions a cannula seal with respect to instrument guide 204 and cannula 202. FIG. 4A illustrates some embodiments of cap 210. FIG. 4A illustrates an embodiment of a cap 210 that has been disassembled. As shown in FIG. 4A, cap 210 includes a lid 402, a locking ring 404, a base 406, and a seal 408. In some embodiments, cap 210 can be formed by mechanically assembling lid 402, locking ring 404, base 406, and seal 408. Assembly (for example, during manufacturing) can be performed without glue, and the parts may be configured as shown to snap together to form cap 210.

As is further illustrated in FIG. 4A, lid 402 includes an instrument guide clip 418. Clip 418 can engage instrument guide 204 to mechanically fasten instrument guide 204 to cap 210, while allowing instrument guide 204 to rotate relative to cannula 202. Such rotation allows the entire cluster of instruments inserted through the instrument guide to rotate as a unit inside cannula 202. Instrument guide clip 418 can also engage receiver 420 on base 406, which helps hold the cap components together.

Locking ring 404 may include a release mechanism 416, which may include a spring 422. Engagement and release mechanism 416 may extend through openings 424 in lid 402 to provide for user release of the cap from the cannula. Engagement and release mechanism 416 also extends through openings 440 in base 406 to hold cap 210 onto cannula 202. The latching tabs 419 are angled so that as the cap 210 is pressed onto cannula 202, locking ring 404 rotates against spring 422 to allow the latching tabs to engage cannula 202, and spring 422 then returns locking ring 404 to a latched position against cannula 202.

Base 406 includes alignment pins 426 that help position cap 210 with respect to cannula 202 so that cap 210 is correctly oriented on cannula 202. In addition, varying quantity or position of alignment pins 426 may be used (three are shown; one individual and two close together) to key a cannula cap 210 to a specific configuration of cannula 202, for example, a specific length cannula in a set of cannulas each having different lengths. Thus a cap improperly configured for a certain cannula is prevented from being latched to such a cannula.

It can be seen that clip 418 on lid 402 releasably engages instrument guide 204, and locking ring 404 releasably engages cannula 202, so that cap 210 holds instrument guide 204 inside cannula 202 and also allows instrument guide 204 to rotate around its longitudinal (long) axis inside cannula 202. Seal 408 is captured between base 406 and lid 402.

Figure 4B:
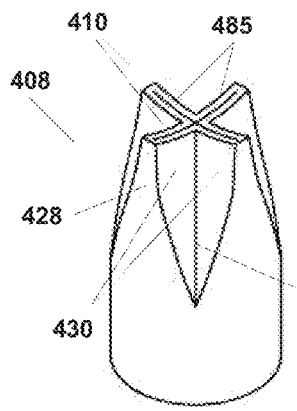
FIGS. 4B-4E illustrate aspects of some embodiments of a cross-slit seal that can be used with many cannulas.

FIGS. 4B, 4C, 4D, and 4E illustrate aspects of a cross slit seal 408 that can be used with some cannulas 202, with or without a cap 210. As shown in FIG. 4B, seal 408 includes a sidewall 428, and sidewall 428 includes four sets of inward folded sidewall panels 430. Each set of sidewall panels 430 intersect one another along panel intersection line 431, and all sidewall panels 430 meet at their ends to form cross slits 410. The ends of the folded sidewall panels 430 come together to form the cross slits 410 in a narrow end surface 485 formed by the ends of the folded sidewall panels 430.

Figure 4C:
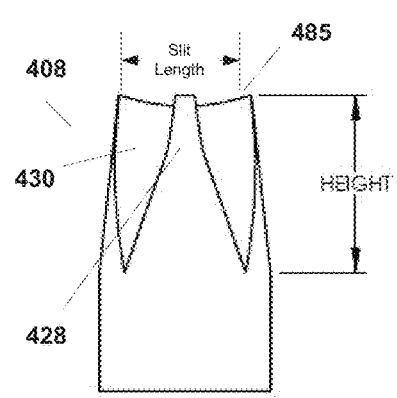

As shown in FIG. 4C, a height of seal 408 can be defined in a longitudinal direction (aligned between top and bottom) between locations on the outer perimeter of seal 408 at which the folded sidewall panels 430 begin and the most distant location on end surfaces 485. The height shown in FIG. 4C is for the seal 408 when closed, with no instrument or device inserted.

In accordance with some embodiments of the invention, the end surfaces 485 are concave (they are shown as a continuous curve but other shapes may be used) when the cross slits 410 are closed. As shown in FIG. 4E, it can be seen that when an object is inserted through the cross slits 410, the folded sidewall panels 430 move away from each other. It can further be seen that the innermost ends 485a of the folded sidewall panels 430, the locations at which the folded sidewall panels 430 contact the object inserted through the slits, are displaced generally upward as the folded sidewalls 430 move outward. Thus the overall height of the cross slit seal 408 increases when an object is inserted. By forming end surfaces 485 to be concave, however, the increase in seal height that results from the inserted object is reduced.

It can also be seen from FIGS. 4C and 4E, that the sidewall 428 tends to move outward when an object is inserted through the slits 410, and by tapering the outer diameter of the seal to be narrow towards slits 410, the outer shoulders 485b of the surfaces 485 can be kept from moving beyond an overall diameter of the closed seal 408.

As shown in FIG. 4C, a slit length can be defined in a lateral direction (aligned from side to side). As an aspect ratio between the seal height and slit length changes with the slit length becoming relatively longer with reference to the seal height, it can be seen that by making end surfaces 485 concave, the increase in seal height with an inserted object is reduced relatively more than the increase in seal height if the end surfaces 485 were not concave. Thus, the seal will be relatively shorter with an inserted object, which keeps the seal from interfering with another longitudinally positioned object and allows an assembly that allows seal 408 to be relatively shorter. This seal height reduction allows the associated configurations of cannula 202 and cap 210 to be similarly shortened, described more fully below. In minimally invasive surgery, even a small change in length (e.g., 1 to 2 mm) can be clinically significant.

Figure 4D:
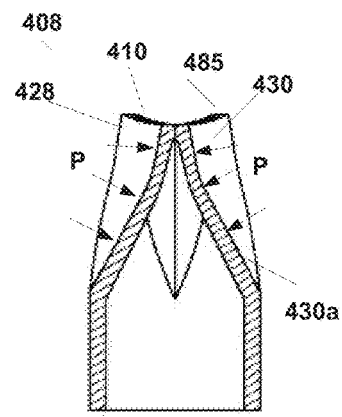
Figure 4E:
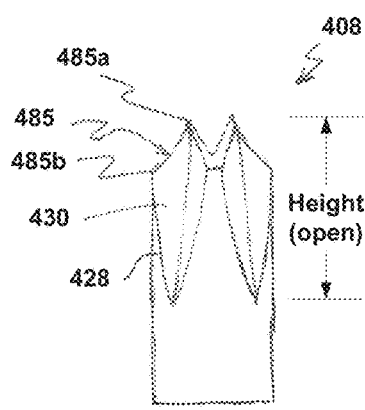

As illustrated in FIG. 4D, the large areas of folded sidewall panels 430 allows pressure P outside seal 408, for example from insufflation, to push slits 410 closed and keep them closed. A large height in relation to slit length provides for seal 408 to be flexible in the region of slits 410 so that relatively low pressures can effectively close seal 408

In some embodiments of the invention, the outer surfaces 430a of the folded sidewall panels 430 are concave. As shown in FIG. 4D, this concave shape assists sealing by allowing pressure against the surfaces 430a towards the outer perimeter of seal 408 to be more nearly aligned with the seal's longitudinal axis, which helps to close the folded sidewall panels 430 against each other, and by allowing pressure against the surfaces 430a near the center of the seal to be more nearly aligned across the slits when the seal is closed, which helps to keep the slits closed when no object is inserted. This curved sidewall panel surface especially helps to close and keep closed the seals 408 having relatively low seal height to slit length aspect ratios (see e.g., FIG. 4H), which are described in more detail below.

As shown in FIG. 4A, in some embodiments seal 408 is captured between lid 402 and base 406. Locking ring 404 can be separately captured between lid 402 and base 406. In some embodiments, seal 408 as illustrated in FIGS. 4B through 4E may be used without a cap 210 by placing directly in a cannula. However, the embodiment of seal 408 illustrated in FIGS. 4B through 4E may have a higher aspect ratio (ratio of seal height to slit length) than is desired for a particular cannula. FIGS. 4F through 4O illustrate embodiments of seal 408 that can be used with cap 210 and that have low seal height to slit length aspect ratios.

As shown in FIGS. 4F-4H, seal 408 includes cross slits 410 and includes generally the features that were illustrated in seal 408 in FIGS. 4B through 4E. Folded sidewall panels 430 intersect to form slits 410. As illustrated in FIG. 4G, a height can be defined by either of sidewall 428 (for an overall height of seal 408) or folded sidewall panels 430 (for a height of the cross slit seal portion of seal 408), and a slit length is defined by the length of slits 410. In the FIG. 4G depiction, the height to slit length aspect ratio is less than about 1:1, and more exactly it is about 1:2. Other aspect ratios less than 1:1 may be used. As described above, the end surfaces 485 in which slits 410 are defined can be concave in order to shorten the seal height with an inserted object. Some embodiments of seal 408 have a slit length larger than the seal height, resulting in shorter folded sidewall panels 430 than that illustrated in embodiments of seal 408 illustrated in FIGS. 4B through 4E. This shortened folded sidewall 430 provides for a small area for outside pressure P to push slits 410 closed, as illustrated in FIG. 4. Additionally, the shortened height and consequent aspect ratio may result in a requirement that the sidewall panels 430 of seal 408 be stiffer to maintain proper shape, and so a high pressure P is needed to sufficiently seal the cross slits closed, as is illustrated in FIG. 4I.

FIG. 4J illustrates an embodiment of seal 408 that includes energizing ribs 414 that can provide force F from interaction with the inner wall of cannula 202 to help close slits 410 and keep them closed. Thus ribs 414 work together with the outside pressure P to close seal 408. As shown, ribs 414 are formed on the sidewall of seal 408, and in the depicted embodiment each rib is generally aligned with an outer end of one of slits 410 so that force from opposing ribs helps to close the corresponding perpendicular slits 410. FIG. 4H shows a cross section of seal 408 and illustrates sealing of slits 410 with concave folded sidewalls 430, as described above. FIGS. 4F-4J also illustrate tapering the cross slit seal outer diameter towards slits 410 to reduce height when open, as described above.

Ribs 414 shown in FIG. 4J help to compensate for potential reduced sealing performance due to the shortened height relative to slit length as compared to seal 408 illustrated in FIGS. 4B-4E. The shortened height of seal 408 can enable the use of a shorter cannula 202 and resultingly shorter surgical instruments 102, 104, 106. Shorter surgical instruments 102, 104, 106 can be easier to clean and package, and can have improved stiffness for better surgical performance. Shorter surgical instruments 102, 104, 106 and shorter cannula 202 can also enable the use of a smaller teleoperated robot 140.

Figure 4K:
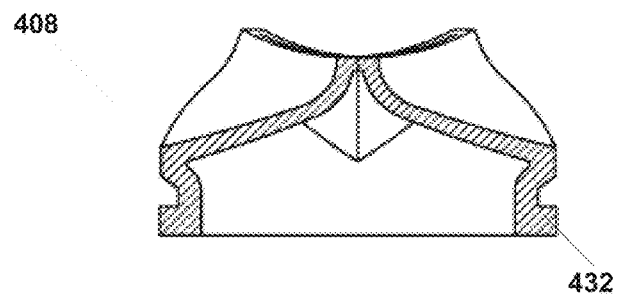
FIGS. 4K-4O illustrate some embodiments of a cross-slit seal that can be utilized with many cannulas.
Figure 4L:
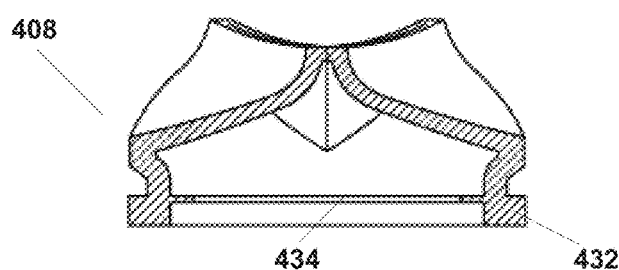
Figure 4M:
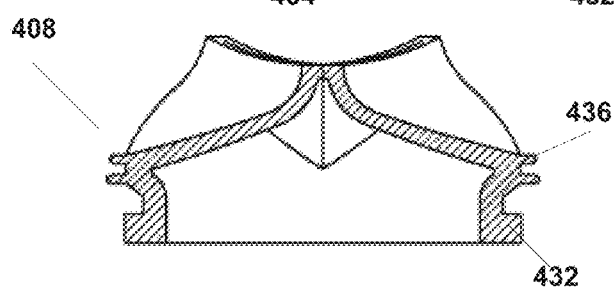
Figure 4N:
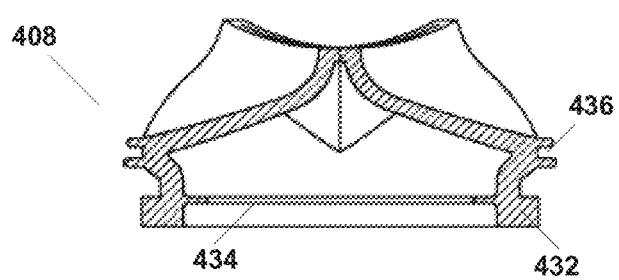

FIGS. 4K through 4O illustrate various features that may be found, separately or combined, in some embodiments of seal 408. FIG. 4K illustrates a seal with a flange 432 that can be used to hold seal 408 in place during installation in cap 210 (or in cannula 202). FIG. 4L illustrates a seal 408 with an integrated inner diaphragm (also known as a lip or septum type) seal 434 that seals against instrument guide 204. FIG. 4M illustrates a seal 408 with an outer seal 436 that seals against the inner wall of cannula 202. FIG. 4M shows outer seal 436 as two annular lip seals and is illustrative of embodiments in which one or more various types of seals may be used to seal against a cannula. FIG. 4N illustrates a seal 408 with both an inner seal 434 and an outer seal 436 so that enhanced seal performance between both a cannula and an inserted object inserted in the cannula is obtained.

Figure 4O:
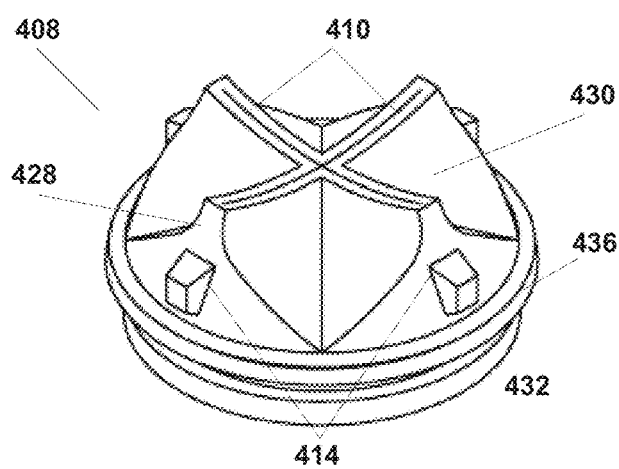

FIG. 4O illustrates a perspective of an embodiment of seal 408. As shown in FIG. 4O, seal 408 includes slits 410, sidewalls 428, and folded sidewall panels 430, energizing ribs 414, flange 432, and outer seal 436. The end surfaces at the cross slits are made concave so that with an object inserted the seal height is less than it would be if the end surfaces were straight across. The concave outer surface of the sidewall panels 430 helps to direct the fluid pressure vector to move the sidewall panels to the closed position and to keep them closed against each other at the cross slits. And, the ribs 414 further help keep the cross slits closed with the stiff sidewall panels required to form the low height to slit length aspect ratio seal.

FIG. 4P illustrates an assembled cap 210 according to some embodiments. As shown in FIG. 4P, engagement and release mechanism 416 includes a button that extends through openings 424 in lid 402 and latch tabs that extend through openings 440 in base 406 and catch against corresponding mating features in the cannula. Seal 408, with slits 410 and energizing ribs 414, is captured between base 406 and lid 402. FIG. 4Q illustrates a cross section plan view from the top of seal 408 and illustrates spring 422 and the inclusion of locking ring 404. FIG. 4R illustrates a side view and illustrates pins 426.

Therefore, FIGS. 4P, 4Q, and 4R illustrate different views of assembled cap 210. As is illustrated, seal 408 can be a cross-slit seal with slits 410. Further, seal 408 can include energizing ribs 414. Engagement and release mechanism 416 is included so that cap 210 can engage cannula 202 and be released from cannula 202. Instrument guide clip 418 is included to allow the instrument guide 204 to be held against the cap 210 and rotate against a top face of the cap 210, and to be resiliently bent away from the instrument guide 204 in order to allow the instrument guide 204 to be released from the cap 210. Thus by moving the locking ring 404, the cap 210 and instrument guide 204 combination can be removed from the cannula 202, and by moving the instrument guide clip 418, the instrument guide 204 can be removed from the cap 210 and cannula 202 combination.

In some embodiments, engagement and release mechanism 416 may be difficult to access when instrument guide 204 is installed. The inaccessibility of engagement and release mechanism 416 can help to prevent unintentional release of cap 210 from cannula 202, which would lead to loss of insufflation pressure. In some embodiments, it is therefore preferred to remove instrument guide 204 from cap 210 before removing cap 210 from cannula 202.

Figures 4S, 4T:
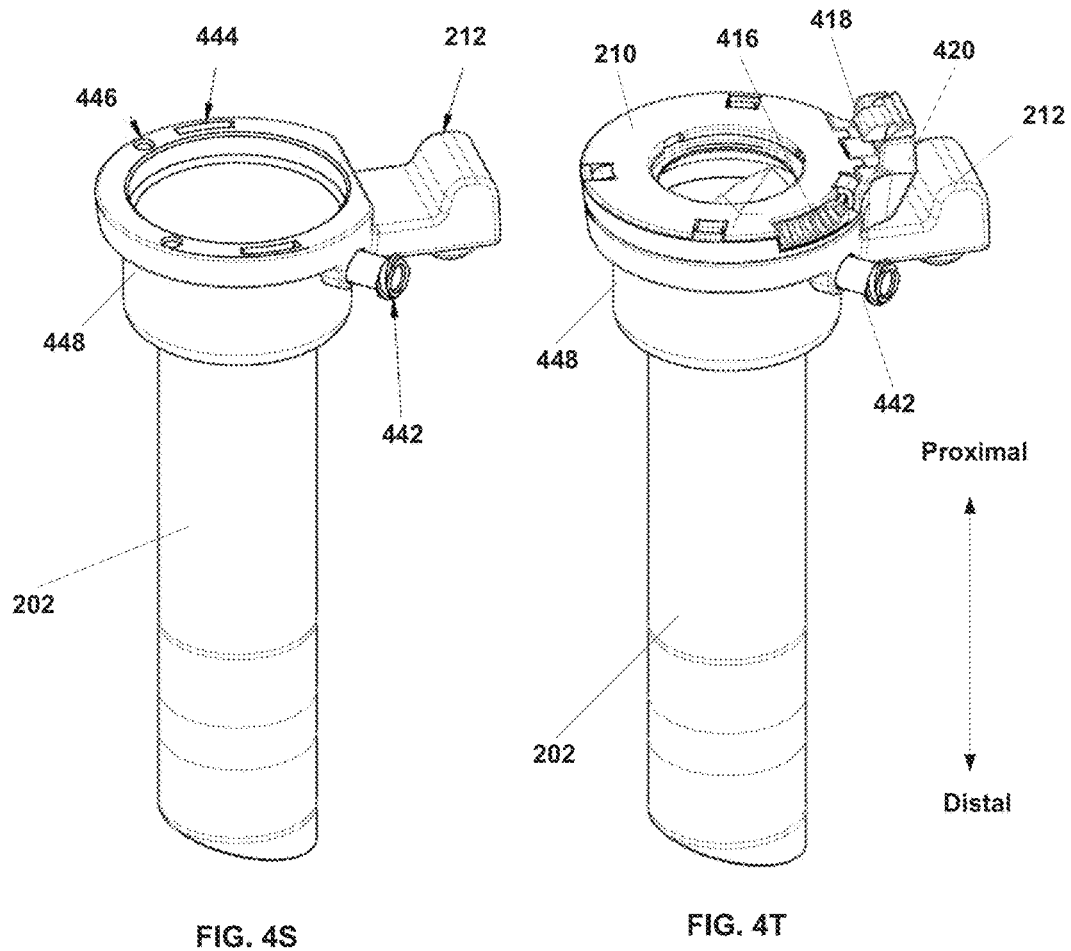
FIGS. 4S and 4T illustrate insertion of an assembled cannula cap and seal into a cannula.

FIGS. 4S and 4T illustrate a cannula 202 and coupling of cap 210 similar to that shown in FIGS. 4K through 4M to cannula 202. As shown in FIG. 4S, cannula 202 includes a receiver 444 that can receive the latch tabs 419 of engagement and release mechanism 416. Further, cannula 202 includes pin receivers 446 that receive pins 426 of cap 210. In some embodiments, the keying feature relationship represented by pin receivers 446 and receive pins 426 can be inverted, with projections on a cannula 202 and receptacles on the cap 210. Further, an insufflation connector 442 can be included to receive insufflation gas from a hose, and seal 408 is shaped to allow gas to flow from connector 442 through the cannula and enter the surgical site (see e.g., FIG. 4U). As shown in FIG. 4T, cap 210 can be attached to cannula 202. Engagement and release mechanism 416 couples cap 210 to cannula 210 in a releasable fashion. As shown in FIG. 4T, clip 418 can align with latch feature 212 on the cannula 202 to create a streamlined perimeter of the assembly. As shown in FIG. 4T, seal 408 resides in cannula bowl 448 of cannula 202.

Figure 4U:
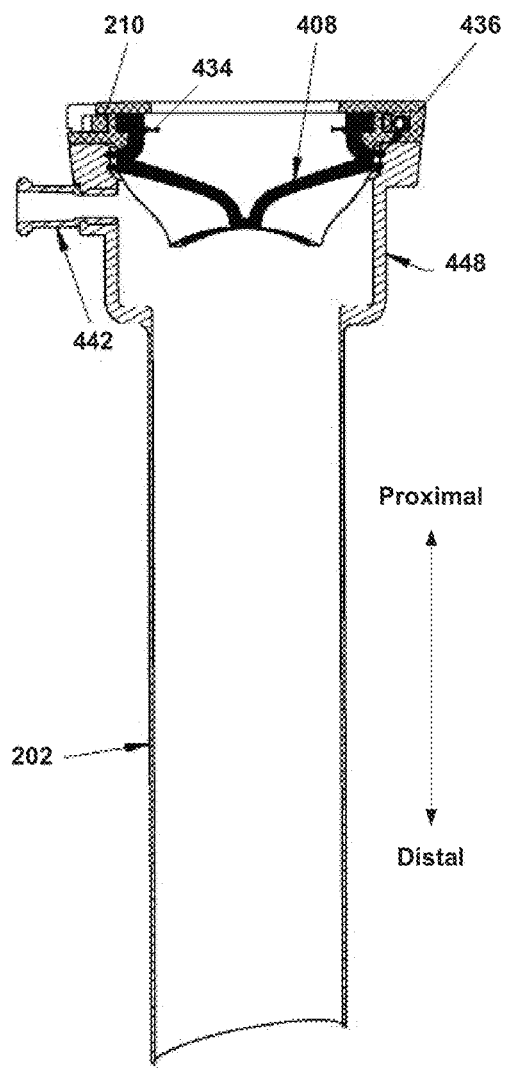
FIGS. 4U and 4V illustrate cross sections of a cannula with inserted cannula cap and seal according to some embodiments of the present invention.
Figure 4V:
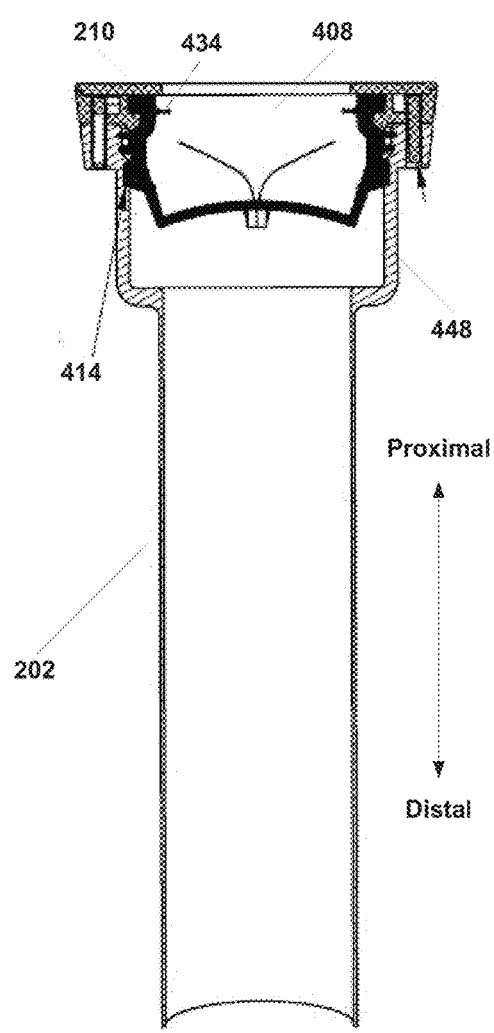

FIGS. 4U and 4V illustrate a cross section of cannula 202 and cap 210. As shown in FIG. 4U, seal 408 inserts into cannula bowl 448 when cap 210 is latched to cannula 202's proximal end. In some embodiments, outer seal 436 seals against an inner wall of the cannula bowl to help prevent insufflation gas escape between the seal's outer wall and the cannula bowl's inner wall. As shown in FIG. 4V (rotated around the longitudinal axis by about 45 degrees from FIG. 4U), energizing ribs 414 engage with the inner wall of cannula bowl 448 to push slits 410 closed. As depicted, the distance between the outer surfaces of ribs on opposite sides of the seal is such that a slight friction fit exists between the ribs and the cannula's inner surface.

Therefore, cap 210 snaps into cannula 202 and can provide a seal against insufflation gas escaping when an object is not inserted in cannula 202. Seal 408, which is a cross slit seal as discussed above, engages the inner diameter walls of cannula 202 so that energizing ribs 414 can help force slits 410 closed. Seal 408, in addition to providing a seal to devices inserted through cannula 202, can also provide a perimeter seal around the top of cannula 202, for example with outer seal 436 integrated with seal 408. The seal 408 has an outer diameter larger than the outer diameter of objects inserted through the seal 408. Therefore, as shown in FIGS. 4U and 4V, the seal is positioned in a proximal end cannula bowl 448, which has an inner diameter larger than the inner diameter of the cannula shaft. The bowl 448 allows the seal 408 to be positioned in the cannula 202 and to flex open while the relatively smaller cannula shaft diameter allows for the minimum possible patient incision length. Further, cap 210 can be mechanically keyed to cannula 210 by engagement mechanism 416 in order to ensure the correct cap 210 and cannula 202 pair is mated and/or ensure the cap 210 is correctly oriented on the cannula 202. Skilled artisans will understand that many possible alternate mechanical configurations may be used to attach the cap 210 to the cannula 202 (e.g., various snaps, bayonet-type or screw-type mounts, locking levers, friction fit configurations, etc.). The embodiments described herein are advantageous for their low height and easy operation by operating room personnel with gloved hands in the tight space between the robotic manipulator and the patient, but other mechanisms can also be used.

Cannula seal 408 also can seal against devices that are inserted through cap 210 in order to prevent insufflation gas from escaping when objects are inserted through the seal. As is illustrated in FIG. 2B, channel portion 208 of instrument guide 204 is inserted through slits 410 of seal 408, and instrument guide 204 can engage lid 402 of cap 210. Seal 408, then, can seal around channel portion 208 with integrated inner seals 434 (FIGS. 4L, 4N). Therefore, when channel portion 208 is not present, energizing ribs 414 force slits 410 closed. When channel portion 208 is inserted through slits 410, inner seals 434 seal against channel portion 208. As illustrated in FIGS. 3A and 3B, seal 408 can also seal against an obturator 302 inserted through cap 210. Other devices may be inserted through the seal into the cannula as well.

Seal 408 seals around the inner circumference of cannula 202 to seal cannula bowl 448. As discussed above, some embodiments of seal 408, for example as illustrated in FIGS. 4B-4E, can have a relatively high aspect ratio (i.e., ratio between the height and the slit length), requiring a long cannula bowl 448, while some embodiments of seal 408, for example as illustrated in FIGS. 4F-4O, can have a low aspect ratio, allowing a shorter cannula bowl 448. Embodiments of seal 408 can have any of the features illustrated in FIGS. 4B-4D. The advantages of the relatively shorter cannula bowl are described elsewhere in this description.

Seal 408 can be formed of any suitably resilient material. For example, seal 408 can be formed of an elastomer material such as silicone, in which the stiffness of the material can be controlled during production. In some embodiments, a parylene coating can be used on seal 408 to reduce friction. Reducing friction can help to prevent seal inversion upon removal of an inserted instrument.

As discussed above, using a soft material for seal 408 can facilitate sealing of slits 410 and works well for seal embodiments with a high aspect ratio. Using a stiffer material helps to keep the shape of seal 408, especially in embodiments with low aspect ratios, and may prevent seal 408 from seal inversion as an inserted device is withdrawn. However, a stiffer material can also reduce the tendency of slits 410 to close and seal. Therefore, the stiffness of the material used to form seal 408 balances the competing concerns of providing a good seal with the ability to keep a shape.

As described above, ribs 414 force slits 410 closed so that seal 408 seals against insufflation gas escaping. Ribs 414 are helpful for closing cross slits 410 of seals 408, which extend into cannula 210, in embodiments of seals 408 formed of stiffer materials. As discussed above, a stiffer material may be used where the width of seal 408 is relatively large compared to the height of seal 408. Ribs 414 increase the effective sealing of cross slits 410 if a stiffer material is used.

Instrument Guide and Seal

Figure 5A:
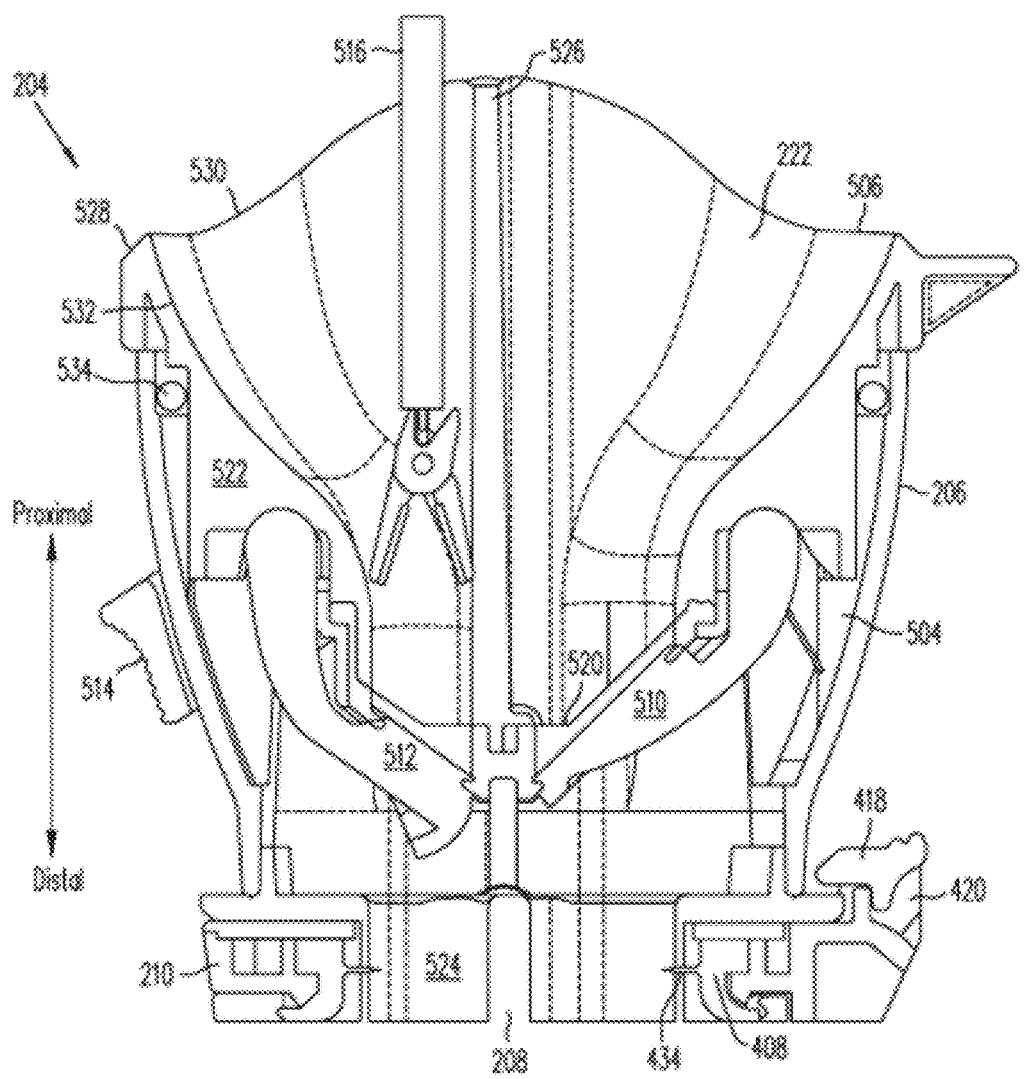
FIG. 5A illustrates an instrument guide coupled with a cap according to some embodiments of the present invention.

In addition to cap 210 being coupled to cannula 202, as described above, instrument guide 204 is coupled to cap 210 so that instrument guide 204, cap 210, and cannula 202 form port 100. FIG. 5A illustrates a cross section of instrument guide 204 engaged with cap 210. As shown, clip 418 allows instrument guide 204 to be mechanically and removably fastened to cap 210. As shown in FIG. 5A, channel portion 208 is inserted through cap 210. A portion of seal 408, seal 434 that as described above seals around channel portion 208, is illustrated in FIG. 5A.

Figure 5B:
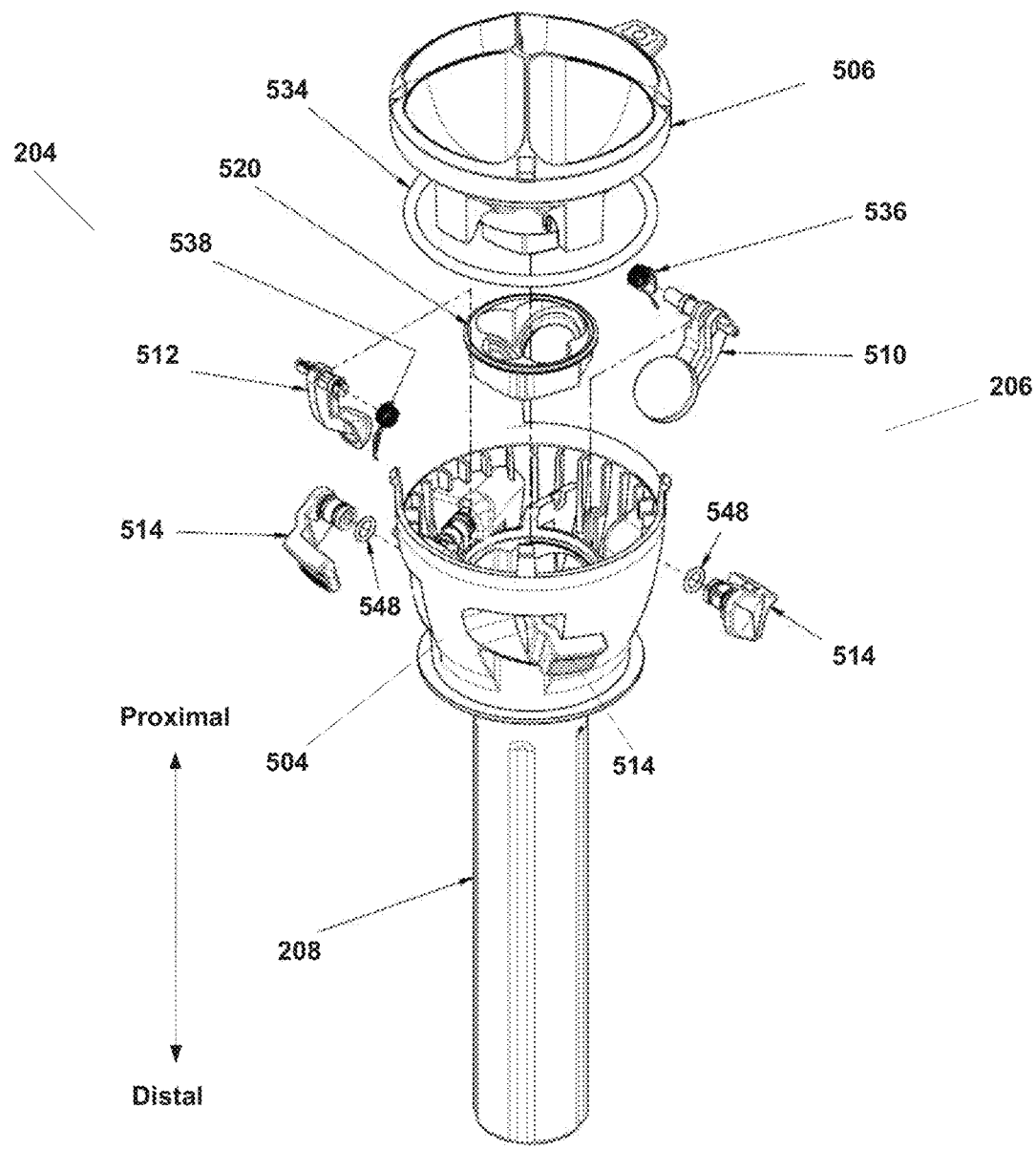

Funnel portion 206 of instrument guide 204 includes lower part 504 and upper part 506. Lower part 504 can be integrally formed (formed as a single piece) with channel portion 208, as shown in FIG. 5B, or it can be separately formed. Upper part 506 engages and can be snapped into lower part 504 during manufacturing.

As described above, when a cannula 210 is inserted into the body and insufflation gas introduced at the surgical site, the gas is prevented from escaping through the empty cannula 210 by one seal feature (the cross slits 410), and the gas is prevented from escaping between the cannula's inner wall and an inserted object by another seal feature (the wipe- or septum-type seal 434 in some embodiments). But since the instrument guide 204 has instrument channels that allow instruments to reach inside the patient, additional seals are needed to prevent insufflation gas from escaping through the instrument channels. And so in the instrument guide, one seal feature prevents the gas from escaping through a channel when no instrument is inserted, and another seal feature prevents gas from escaping between the channel's inner wall and the instrument when an instrument is inserted in the channel.

As shown in FIGS. 5A and 5B, an instrument seal 520 is captured between upper part 506 and lower part 504. Instrument seal 520 engages with doors 510 and 512, which open when an instrument 516 is inserted through funnel portion 206 into channel portion 208. In some embodiments, doors 512 and 510 can be mechanically opened, for example door 512 can be opened with an actuator 514, so that an operator can independently operate door 512. Instrument seal 520 seals against doors 512 and 510 when no instrument 516 is in place and seals against instrument 516 when instrument 516 is inserted.

Each of the openings in seal 520 is sized and shaped to accommodate an associated instrument outer diameter, and the corresponding door is sized and shaped to seal against the opening. As is illustrated in FIG. 5A, door 510 is a larger door than is door 512. In many applications, a relatively larger outer diameter camera instrument may be inserted through door 510 and relatively smaller outer diameter surgical instruments 516 are each inserted through one of doors 512.

Seal 408, discussed above, and seal 520 can be formed of any sealing material, including silicone or other substances. Further, seals 408 and 520 can be of any suitable stiffness. In some embodiments, seals 408 and 520 can be coated with a lubricant, for example parylene, to reduce friction.

As shown in FIG. 5A, in some embodiments instrument seal 520 can be a pyramidal-shaped seal where doors 510 and 512 engage seal 520 at an angle. Doors 510 and 512, therefore, can open and close by following a low arc that utilizes less lengthwise space in lower part 504. Further, the sealing area between doors 510 and 512 and seal 520 can be significantly increased by the angled aspect of instrument seal 520, which may result in more effective sealing.

As shown in FIG. 5A, upper part 506 of funnel portion 206 includes funnel guides 530 and 222 that receive instruments such as instrument 516. Funnel guide 530, which is one of funnel guides 224, 226, or 228 illustrated in FIG. 2C, guides instruments to one of doors 512. Funnel guide 222 guides instruments, usually an endoscope, to door 510. As shown in FIG. 5A, funnel guide 530 can include a concave surface 532 that captures the tip of an instrument 516. Concave surface 532 transitions to a convex surface 522, which guides instrument 516 through door 512 and into a corresponding channel 524 of channel portion 208. Funnel guide 222 is shaped similarly to funnel guide 530. The center 526 of upper section 506 is raised above the outside edge 528 of upper part 506, creating a convex shape to the top of upper part 506. This convex shape increases the effective size of the opening of funnel guide 530, making it easier to aim instrument 516 into the correct channel, channel 524, of channel portion 208 during instrument loading.

As discussed above, seal 408 seals against insufflation gas loss along the outer diameter of channel portion 208. Seal 520 seals either against doors 512 and 510 or against an instrument, such as instrument 516 illustrated in FIG. 5A. Therefore, access port 100 is substantially sealed to prevent insufflation gas pressure loss at the surgical site as an instrument guide or other object is inserted or removed from the cannula and as one or more instruments or other objects are inserted or removed from the instrument guide.

FIG. 5B is an exploded perspective view that illustrates an embodiment of instrument guide 204. As shown in FIG. 5B, lower part 504 can be integrally formed with channel portion 208. Doors 510 and 512 and levers 514 can be inserted and mechanically coupled in lower part 504. As is further shown in FIG. 5B, doors 510 and 512 may be spring loaded and biased to the closed position against seal 520 with springs 536 and 538, respectively. Further, levers 514 may be sealed from the insufflation gas by O-rings 548. Seal 520 can be seated appropriately into lower part 504, and upper part 506 can then be inserted and fixed into place against lower part 504. An O-ring 534 can seal between upper part 506 and lower part 504.

Figure 5C:
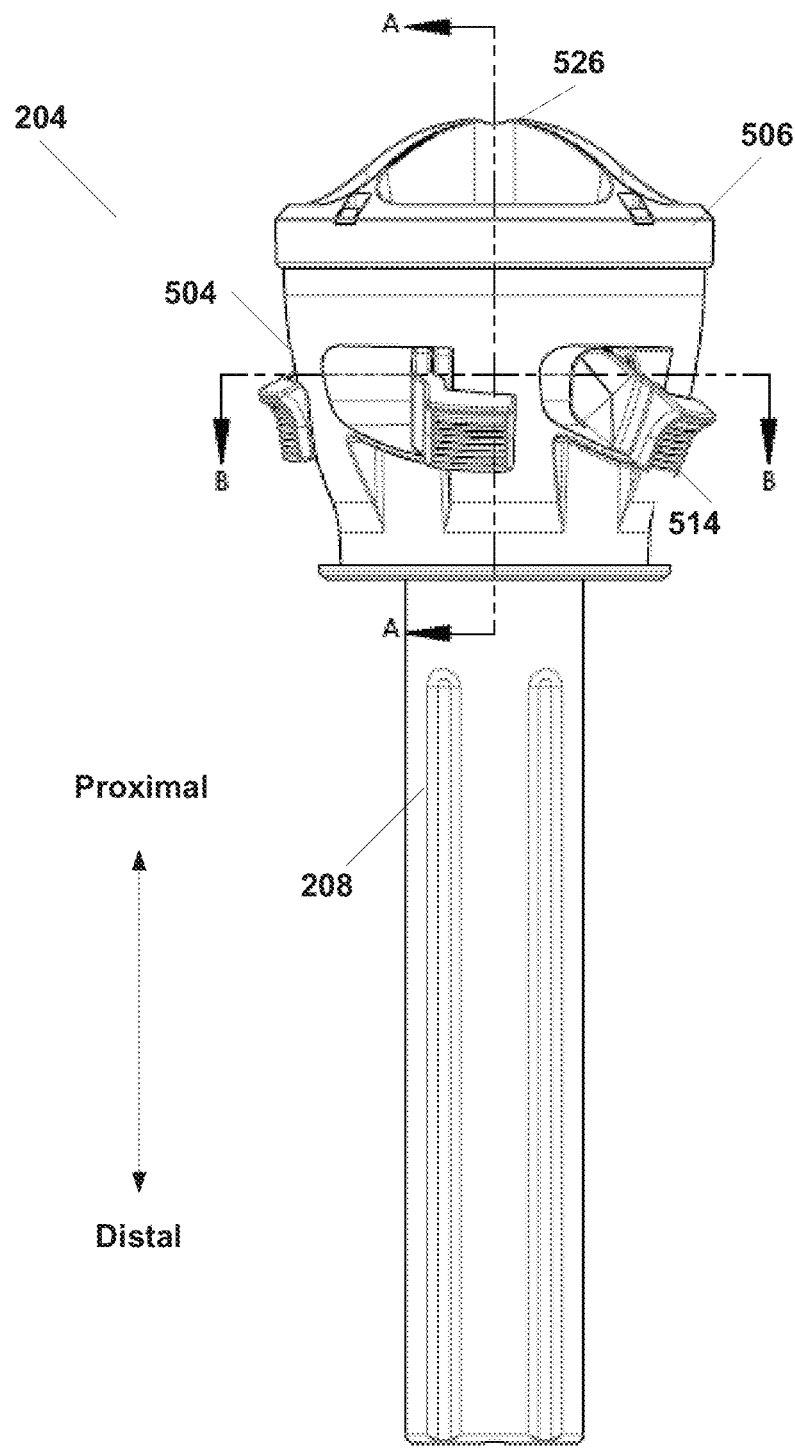

FIG. 5C illustrates an assembled instrument guide 204 as illustrated in FIG. 5B. FIG. 5C illustrates the convex nature of center walls 526 of upper part 506, which help guide instrument tips into the correct individual instrument guide channels during instrument insertion. Further, FIG. 5C illustrates multiple levers 514, one for each of doors 510 and 512 (not shown).

Figure 5D:
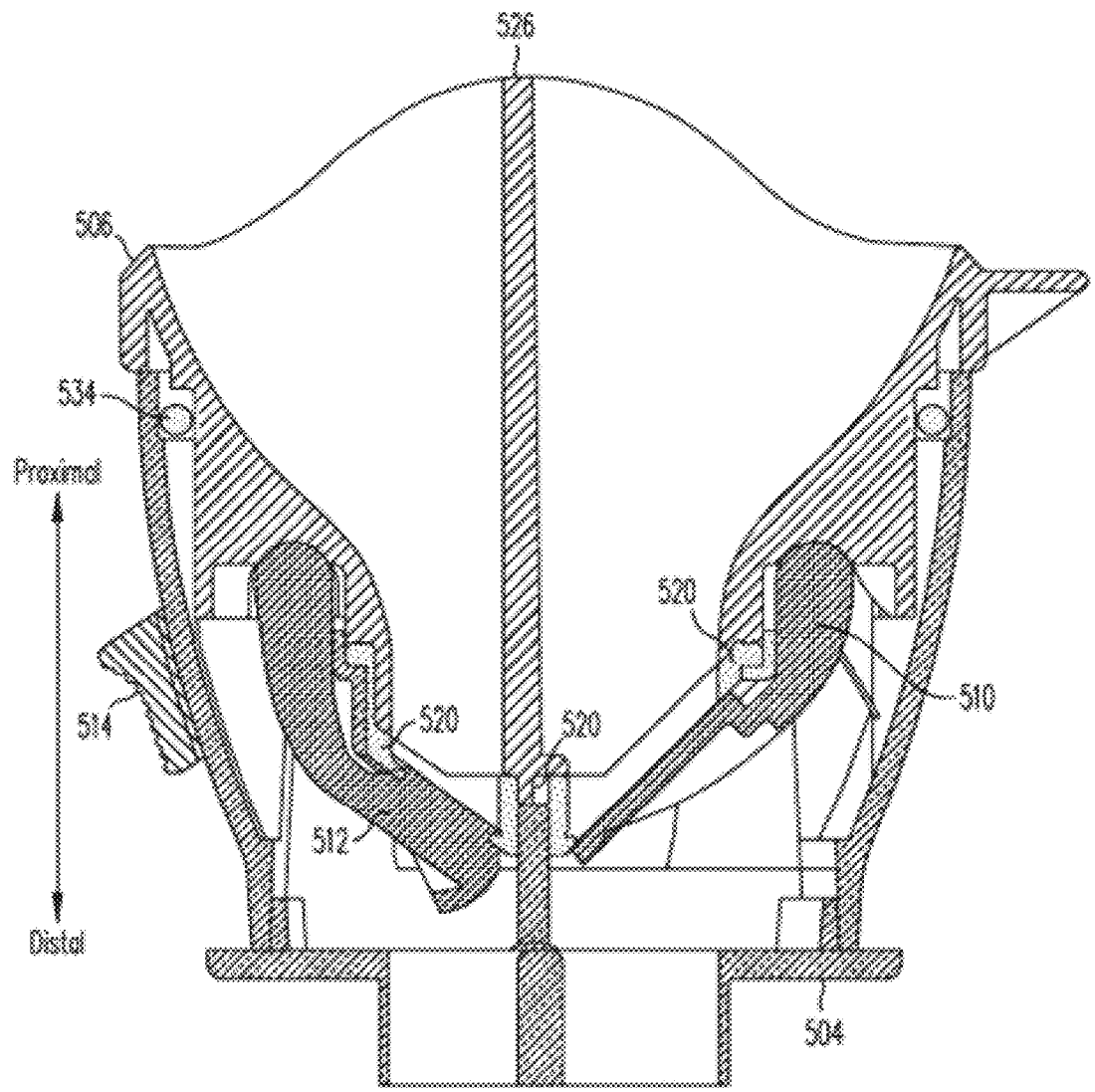

FIG. 5D illustrates a cross sectional view along the A-A direction of instrument guide 204 as illustrated in FIG. 5C. FIG. 5D illustrates doors 510 and 512 seated against seal 520. Further, FIG. 5D illustrates O-ring 534 between lower part 504 and upper part 506.

FIG. 5E illustrate a cross section along the B-B direction of instrument guide 204 as illustrated in FIG. 5C. FIG. 5E illustrates mechanical connection 550 between levers 514 and doors 510 and 512, as well as mounts 552 that receive and support doors 510 and 512 in lower part 504.

Figure 6A:
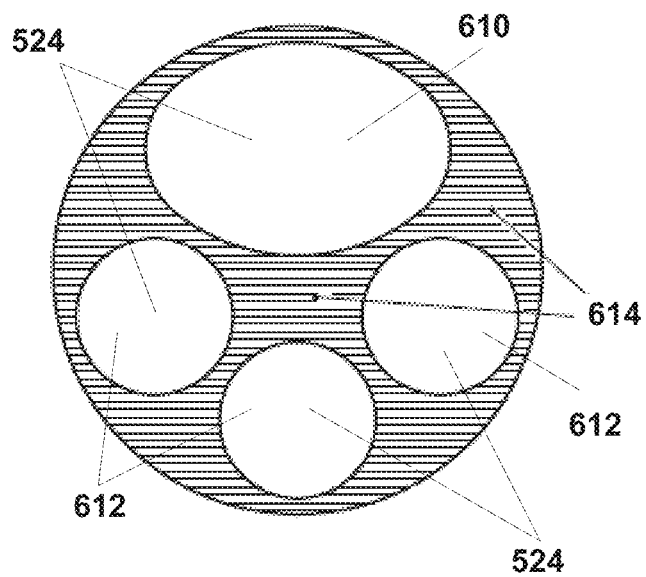
FIGS. 6A and 6B illustrate cross sections of embodiments of a channel portion of the instrument guide.
Figure 6B:
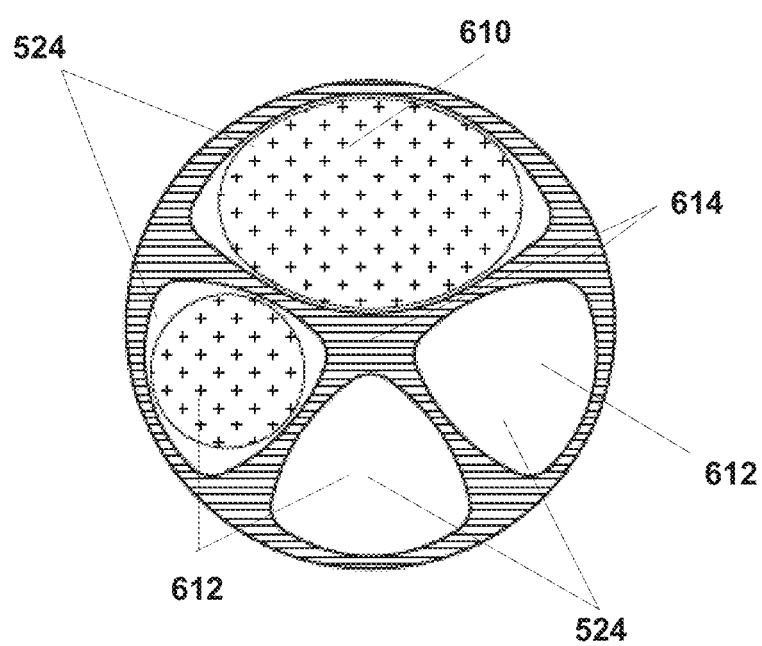

FIGS. 6A and 6B are two illustrative cross sections of channel portion 208. Channel portion 208 is shown with four illustrative instrument channels 524 (more or fewer channels may be used in other embodiments). The channels 524 may also be termed lumens, and in some embodiments channels 524 are not completely enclosed. The cross sections of each of the channels 524 are sized and shaped to provide adequate support for an instrument shaft as the shaft is inserted through channel portion 208 and to allow channel portion 208 to be formed by molding for easy manufacturing. As shown in FIG. 6A, channels 524 include a camera channel 610 and three instrument channels 612. Camera channel 610 is larger and differently shaped than instrument channels 612 to accommodate the individual camera instrument cross section. A similar modification may be made to one or more of the instrument channels to accommodate various instrument cross section sizes and shapes. In the embodiments of channel portion 208 illustrated in FIG. 6A, the cross section of camera channel 610 is oblong and the cross sections of instrument channels 612 are circular to approximate the actual cross sections of the instruments. This arrangement may result in thick areas 614 in channel portion 208, which may cause injection molding problems, such as sinks, voids, and distortions during production. In order to reduce injection molding problems, the individual channel cross sections are shaped to produce a more uniform wall thicknesses in channel portion 208. FIG. 6B illustrates an alternate embodiment in which the camera channel 610 cross section has a more extended oblong shape and the instrument channel 612 cross sections have rounded triangular shapes. This design results in less thick areas 614, which improves injection molding results during manufacturing, while still supporting surgical and camera instruments.

Figure 7B:
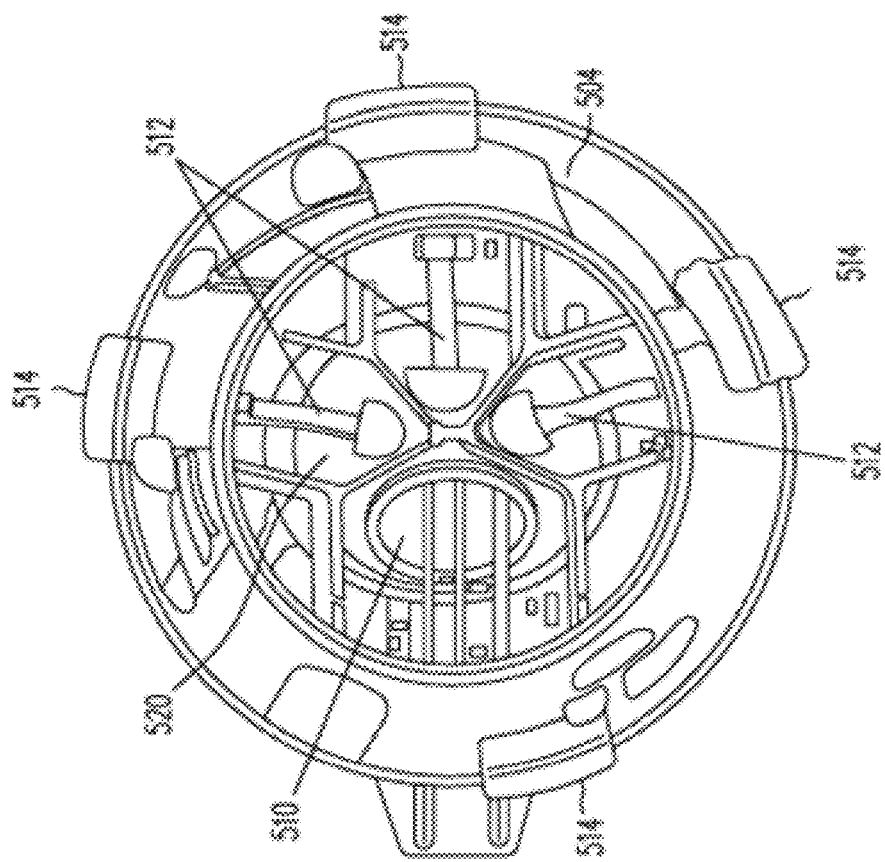
FIGS. 7A and 7B illustrate an instrument seal according to some embodiments of the present invention.
Figure 7A:
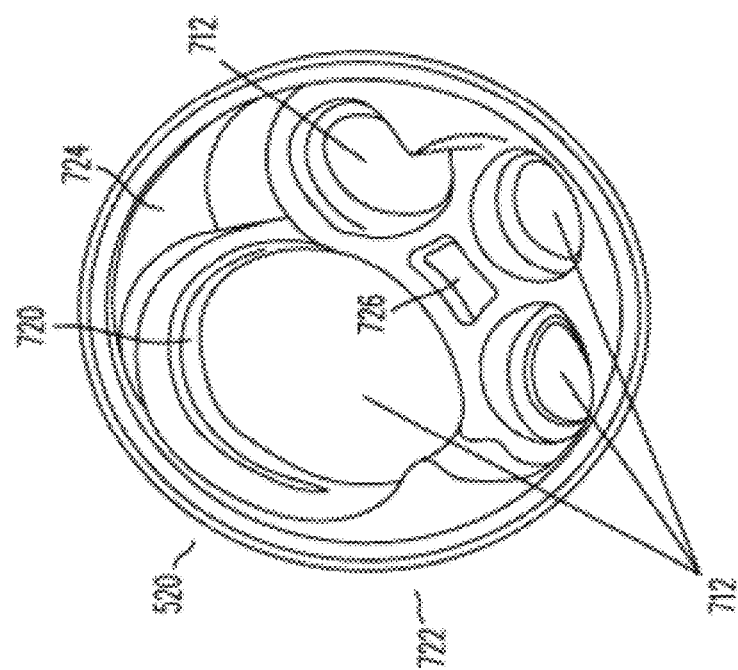

FIG. 7A is a top perspective view of an embodiment of seal 520, and FIG. 7B is a bottom view of lower part 504. The embodiment of seal 520 illustrated in FIG. 7A is a pyramid-shaped seal with openings 712 that align with and match the shapes of channels 524. As such, openings 712 are shaped to accommodate the shapes of channels 524. As shown in FIG. 7B, lower part 504 includes door 510 and doors 512 that seal against openings 712 in seal 520.

Figure 7C:
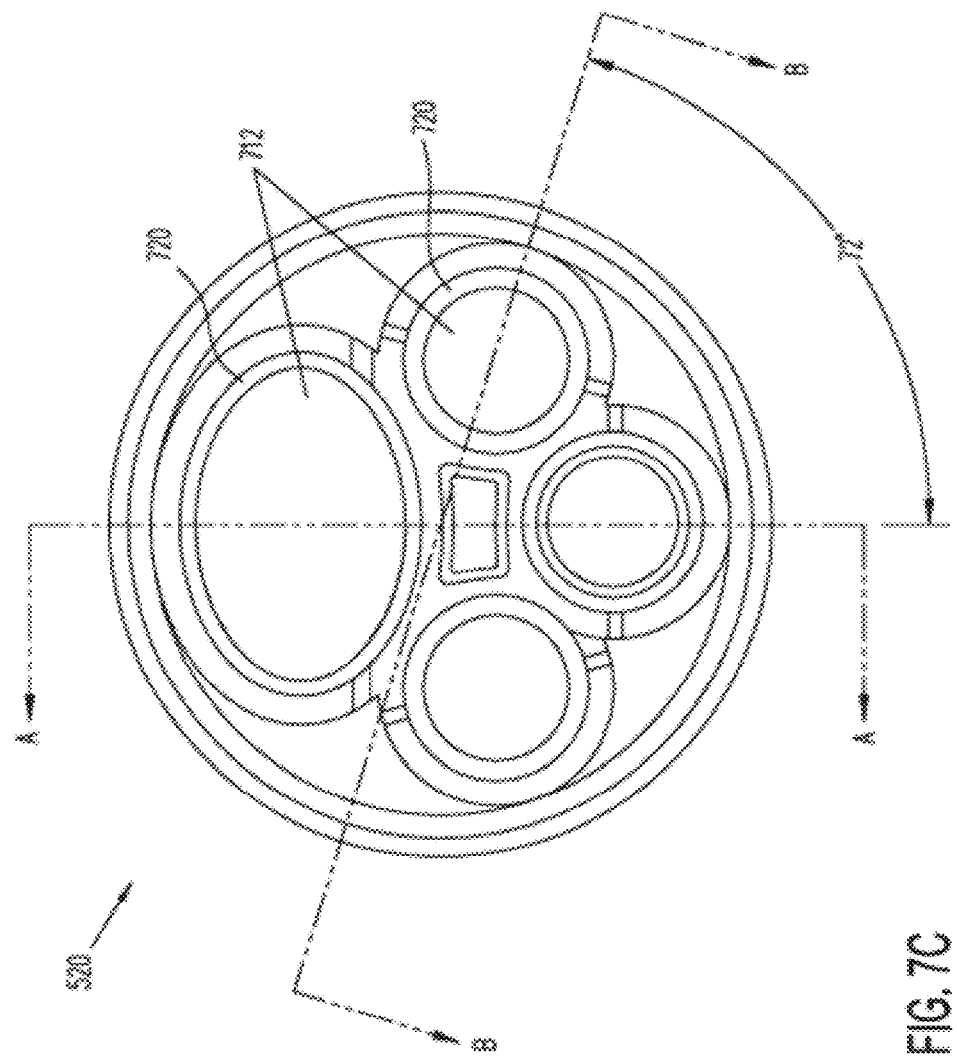

FIG. 7C illustrates a top view of an instrument seal 520. As is shown, openings 712 include a large opening appropriate for a camera channel 610 and three small openings appropriate for instrument channels 612. Lips 720 around openings 712 can seal around the shafts of instruments 516 and can provide a seat to seal against doors 510 and 512. In some embodiments, as discussed further below, seal 520 can include two parts that respectively seal against doors 510 and 512 and the shaft of an instrument 516.

FIGS. 7D and 7E show cross sections of an embodiment of instrument seal 520 along the directions A-A and B-B shown in FIG. 7C, respectively. FIGS. 7D and 7E illustrate how in some embodiments the openings 712 are formed in flat faces of the seal's general pyramid shape. It can be seen that each opening is sized and shaped to seal against an instrument inserted through the opening. For example, if an instrument shaft has a circular cross section, then the corresponding opening 712 is shaped as an ellipse in a plane that bisects the instrument shaft at the angle of the pyramid face to the instrument shaft axis. Therefore, as illustrated in FIG. 7C, the opening 712 appears circular when viewed along instrument shaft axis, and the lip of the opening seals against the instrument shaft. The elliptical opening shape is useful for cylindrical instruments that roll around the instrument shaft axis. It should be understood that although several seal 520 embodiments are described as generally pyramid-shaped, other shapes may be used. For example, a concave dome shape or other concave shape may be used, and the openings 712 are formed in a continuously curving surface.

Figure 7F:
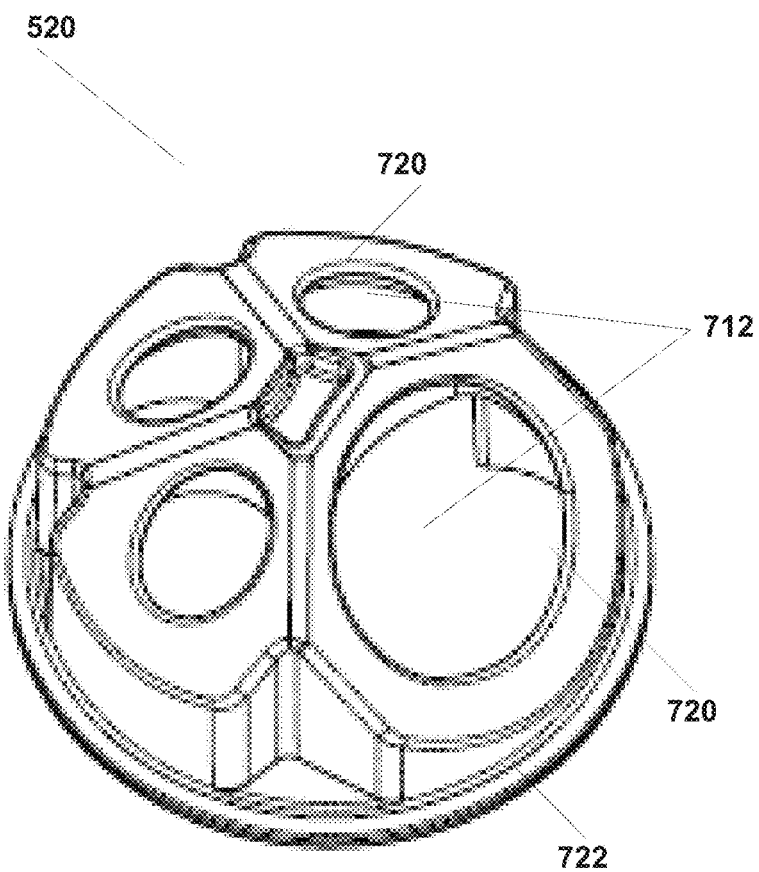
FIGS. 7F and 7G illustrate top and bottom perspective views of an instrument seal as shown in FIG. 7A.
Figure 7G:
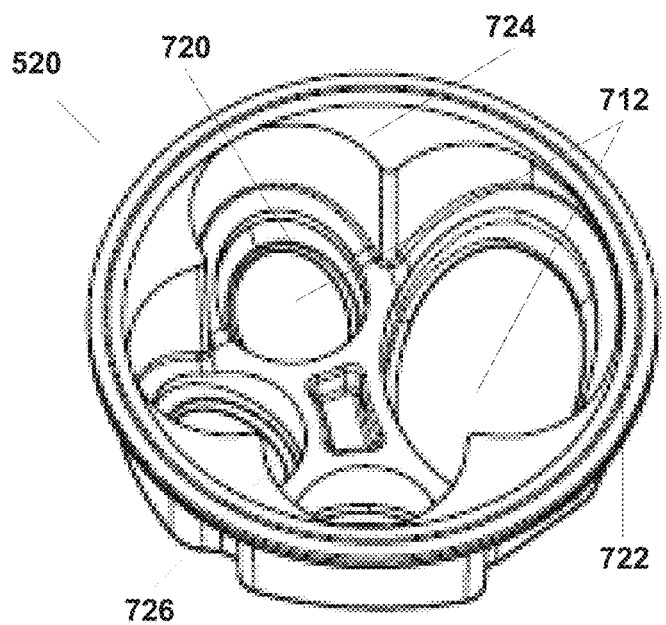

FIGS. 7F and 7G illustrates top and bottom perspective views of an embodiment of instrument seal 520 and further illustrate the general pyramid shape. As is further illustrated, an outer lip 722 can seal between the instrument guide's lower part 504 and upper part 506 so that a seal is established between the instrument guide and the seal 520 body. Structures 724 and 726 can help position and align instrument seal 520 between lower part 504 and upper part 506 so that openings 712 are appropriately positioned.

Figure 7H:
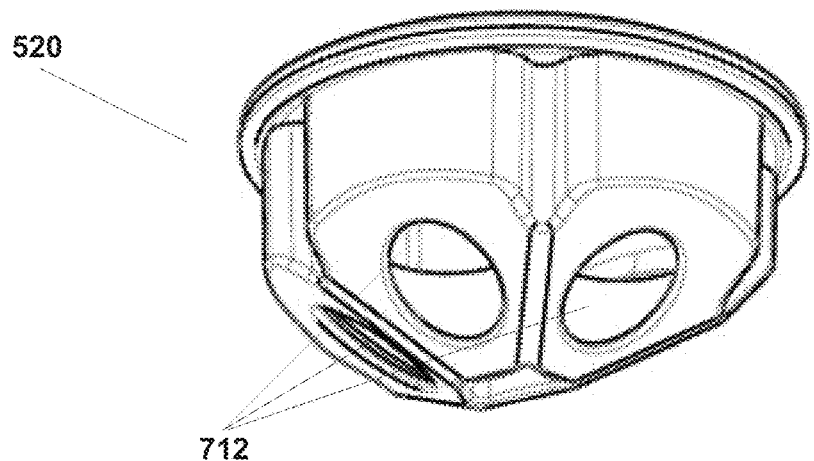
FIGS. 7H and 7I illustrate an embodiment of an instrument seal.
Figure 7I:
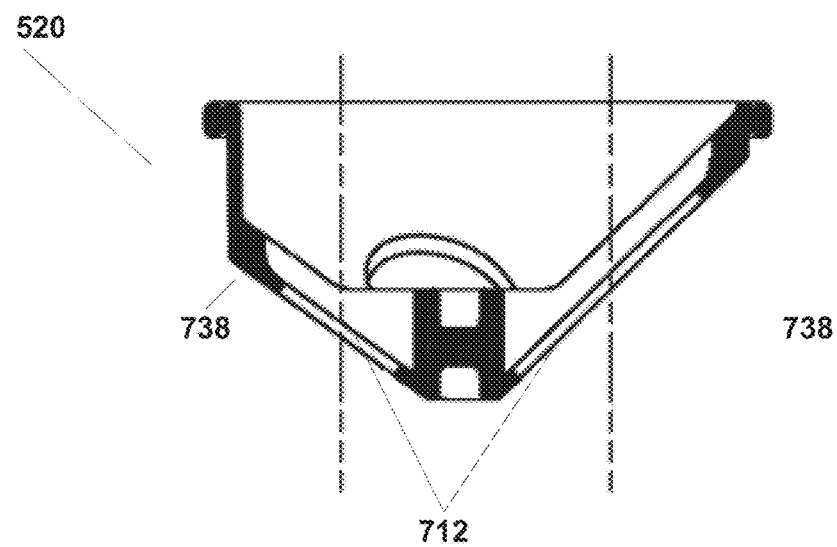

FIGS. 7H and 7I illustrate another embodiment of a single-piece instrument seal 520. Instrument seal 520 as illustrated in FIGS. 7C through 7G is pyramid shaped and, as discussed above, is positioned between lower part 504 and upper part 506. As illustrated in FIG. 7I, seal 520 does not include lips 720 around openings 712 that seal against the shaft of an instrument. Instead, a door seal 738 seals against doors 510 and 512 that are positioned in lower port 504 and further is sized to seal against the shaft of an inserted instrument.

In the instrument seal 520 embodiments described so far, each opening is used to both seal against an instrument shaft and to provide a seat against which a door seals. In other embodiments, separate aligned openings may be used so that one opening seals against the instrument shaft and another opening provides the seat for the door. The separate opening may be formed in two different pieces, or they may be formed in a single piece.

FIGS. 7J and 7K illustrate another embodiment of seal 520. The embodiment of seal 520 illustrated in FIG. 7J includes two parts: a door seal 730 and a shaft seal 732. Door seal 730 is a flat lip seal that is positioned between the instrument guide's lower part 504 and upper part 506, as discussed above. Door seal 730 then seals against doors 510 and 512 as discussed above. Shaft seal 732 is positioned in the instrument guide's lower part 504 to seal against the shaft of an instrument.

FIG. 7K illustrates a cross section of an embodiment of seal 520. As shown in FIG. 7K, openings 712a of door seal 730 and openings 712b of shaft seal 732 are aligned so that instruments pass through door seal 730 and shaft seal 732 seals against the shaft of the instrument. Each opening 712a is sized and shaped to seal against a corresponding door (not shown). Openings 712b of shaft seal 732 are sized and shaped appropriately to seal against the shaft of the instrument. As illustrated in FIG. 7J, protrusions 734 molded into door seal 730 can be used to position and align door seal 730 in instrument guide 204. Structure 736 in shaft seal 732 can be used to position and align shaft seal 732 in instrument guide 204.

Figure 7L:
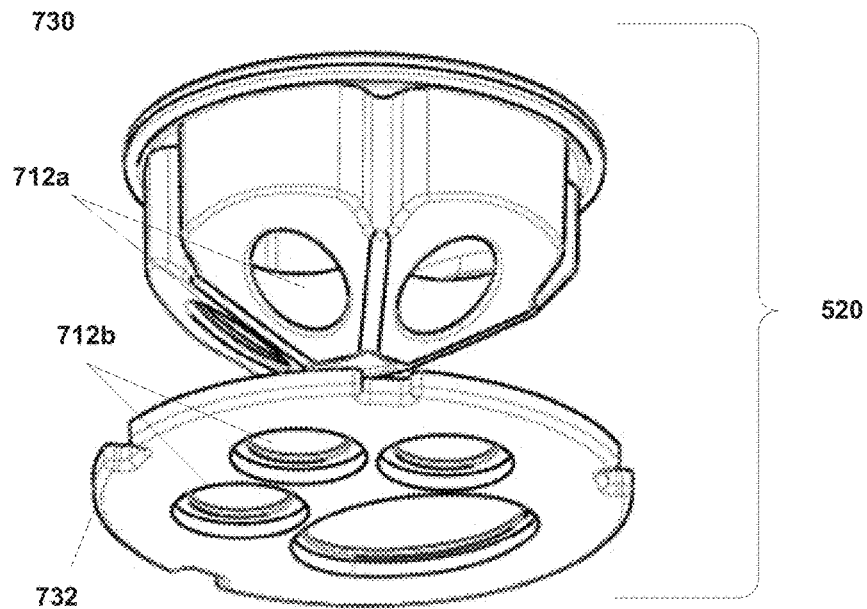
FIGS. 7L and 7M illustrate another embodiment of an instrument seal.
Figure 7M:
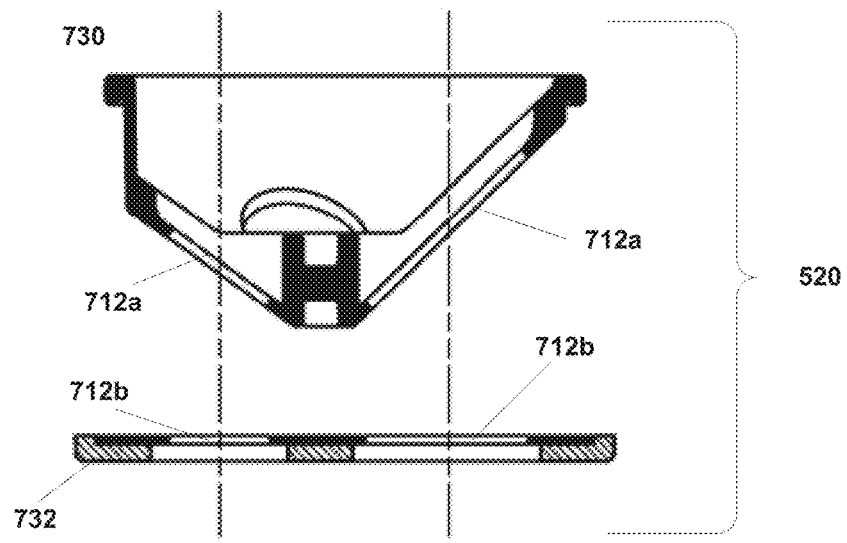

FIGS. 7L and 7M illustrate another embodiment of seal 520. The embodiment of seal 520 illustrated in FIG. 7L includes two parts: a door seal 730 and a shaft seal 732. In the embodiment illustrated 7L, door seal 730 is a pyramid seal similar to that shown in FIGS. 7A through 7I. Shaft seal 732 is a flat lip seal that engages the shaft of an instrument. As discussed above, door seal 730 is positioned between the instrument guide's lower part 504 and upper part 506 and seals against door 510 and doors 512, as discussed above. Shaft seal 732 is positioned in the instrument guide's lower part 504 to seal against the shaft of an instrument. Openings 712b of shaft seal 732 are sized appropriately to seal against the shaft of the instrument. It can be seen that an opening 712a in door seal 730 may also be sized and shaped to seal against an instrument shaft so that two openings 712a and 712b provide a seal against an instrument shaft and one of the two openings 712a provides the seal against the door.

FIG. 7M illustrates a cross section of the embodiment of seal 520 illustrated in FIG. 7L. Door seal 730 and shaft seal 732 are positioned relative to one another such that openings 712a and 712b are aligned with each other and with channels 610 and 612.

Figure 7N:
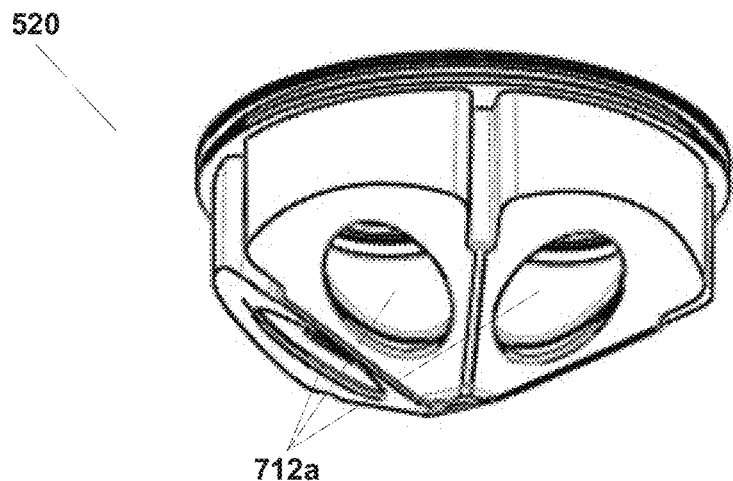
FIGS. 7N and 7O illustrate another embodiment of an instrument seal.
Figure 7O:
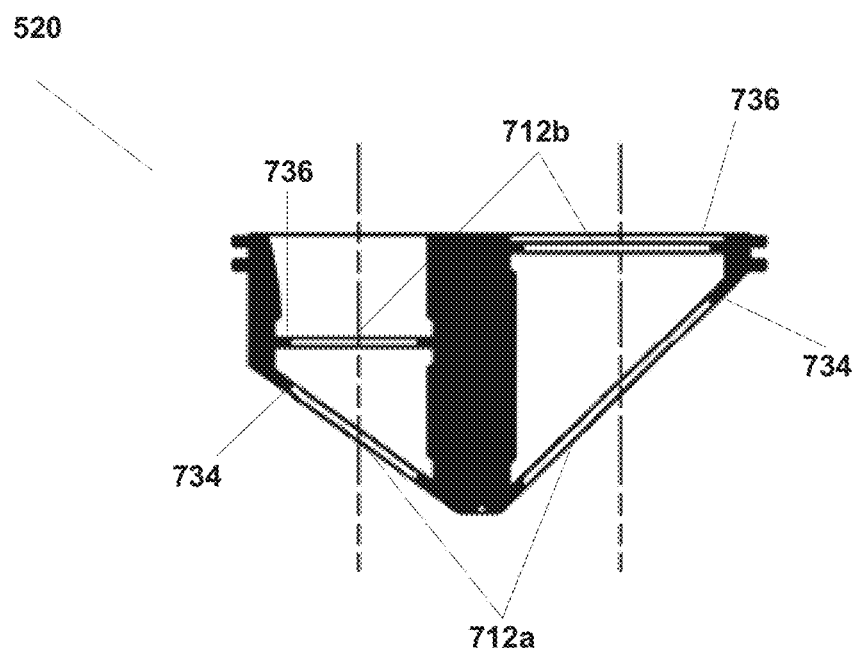

FIGS. 7N and 7O illustrate a single-piece embodiment of instrument seal 520 that incorporates separate door and instrument shaft seal aspects. Instrument seal 520 as illustrated in FIGS. 7N and 7O is pyramid shaped, although other shapes may be used, as discussed above. As discussed above, instrument seal 520 is positioned between the instrument guide's lower part 504 and upper part 506. As illustrated in FIG. 7O, seal 520 includes a door seal part 734 and an instrument shaft seal part 736 associated with each instrument channel in the instrument guide. The door seal part 734 includes openings 712a and seals against door 510 and doors 512 that are positioned in the instrument guide's lower part 504. The instrument shaft seal part 736 includes openings 712b and seals against the shafts of inserted instruments. FIGS. 7N and 7O further illustrate that in double seal embodiments the door seals may be positioned distally of the shaft seals, as with the single seal embodiments illustrated in FIGS. 7A and 7C-7G, and in contrast with previously described double seal embodiments in which the door seals are positioned proximally of the shaft seals.

Referring again to FIG. 7B, door 510 can be larger than doors 512 in order to accommodate a camera instrument, which is typically larger than a tissue manipulation instrument, or other specially sized instrument. As illustrated in FIGS. 7A and 7B, seal 520 seals against door 510 and doors 512, which are spring loaded to seat against the seal 520 openings. Further, seal 520 seals against instruments that are inserted through openings 712. As is further illustrated in FIG. 7B, the instrument guide's lower part 504 includes levers 514 that allow an operator to open each of door 510 and doors 512. An operator can then manually open any of door 510 or doors 512 to allow for insertion of an instrument, or hold open any of door 510 or doors 512 open to allow an instrument to be removed through one of openings 712.

In some embodiments, levers 514 are not directly affected by opening of door 510 or doors 512. In such embodiments, levers 514 are not rigidly keyed to the movement of doors 510 and 512, so that if a door 510, 512 opens, the corresponding lever does not move. Therefore, doors 510 and 512 do not fight the friction of activating levers 514 (e.g., friction from O-rings around the levers). Additionally, because levers 514 do not move when doors 510 and 512 open, it is less likely that any of doors 510 and 512 might get jammed or broken because an lever 514 becomes limited in motion as an instrument, such as instrument 516, is being installed.

Figure 8B:
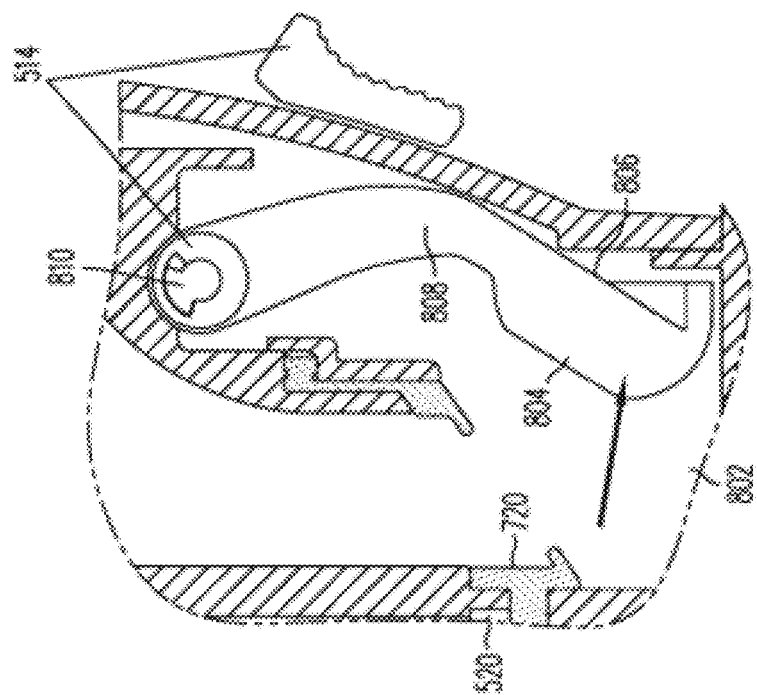
Figure 8A:
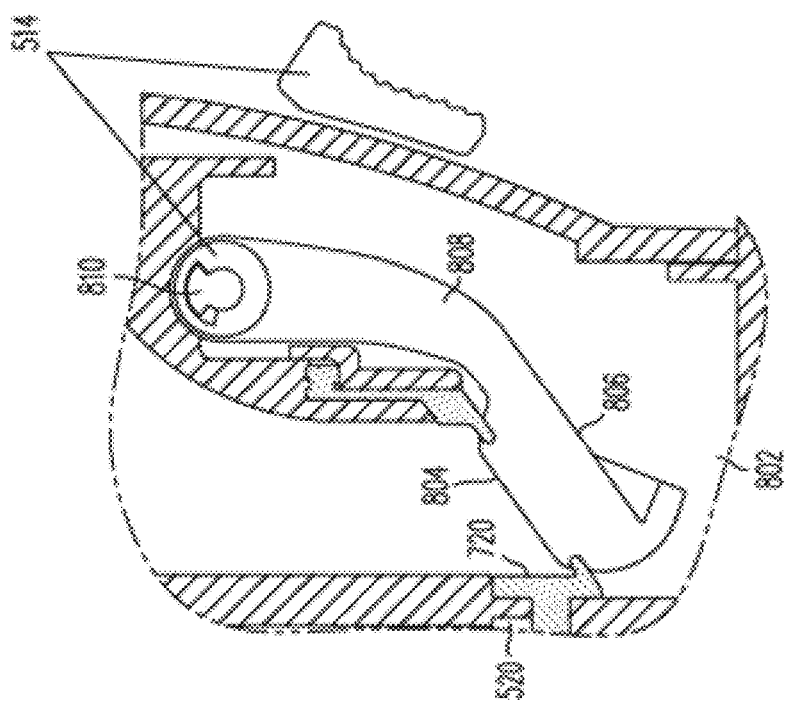

FIGS. 8A-8D illustrate operation of a door mechanism 802 according to some embodiments of the present invention. The door mechanism 802 shown in FIG. 8A can be one of doors 510 and 512. As shown in FIG. 8A, door mechanism 802 includes a sealing part 804 that engages against lip 720 of seal 520, a body part 806 that forms sealing part 804, a pivot part 810, and an arm 808 that connects pivot part 810 with body part 806. Lever 514 is linked to arm 808 as described in more detail below. FIG. 8A illustrates door mechanism 802 in a closed position against seal 520. FIG. 8B illustrates opening of door mechanism 802 through insertion of an instrument (not shown). As shown in FIG. 8B, the instrument pushes door mechanism 802 open while lever 514 remains stationary. Since inserting an instrument moves arm 808 but does not move lever 514, the force required to insert an instrument is only enough to counteract arm 808's torque against seal 520, and so instrument insertion is made easier.

FIGS. 8C and 8D illustrate opening of door 802 with lever 514. As shown in FIG. 8D, lever 514 is mechanically coupled to engage door mechanism 802 at pivot 810. As such, lever 514 and door mechanism 802 include a common pivot axis. The mating configuration allows door mechanism 802 to swing open without activating or otherwise affecting lever 514 as shown in FIG. 8B. However, if lever 514 is rotated, door mechanism 802 is engaged at pivot 810, and door mechanism 802 is opened. As shown in FIG. 8D, pivot 810 includes a center shaft 812 that is mechanically connected to door 802. A dog 814 is connected to center shaft 812 such that it can engage with lever 514 during certain rotations of lever 514. If pivot 810 is rotated to open door 802, dog 814 may not engage lever 514. However, if lever 514 is rotated to open door 802, dog 814 is engaged with lever 514. Therefore, pivot 810 of door mechanism 802 can rotate open without contacting lever 514. However, rotating lever 514 engages door mechanism 802 at pivot 810 to open door mechanism 802. It can be seen that by altering the engagement angles between the door and the lever, when an instrument is inserted and holding a door open, the lever can cause a small additional rotation to the door to completely disengage the arm 808 from the instrument shaft.

Figure 9A:
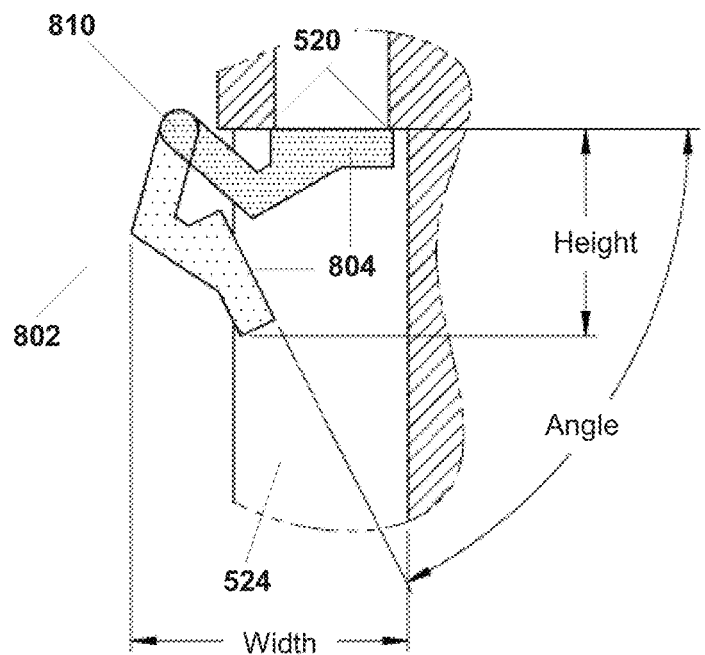
FIGS. 9A and 9B illustrate the relationship between seal angle and door opening angle in doors according to some embodiments of the present invention.
Figure 9B:
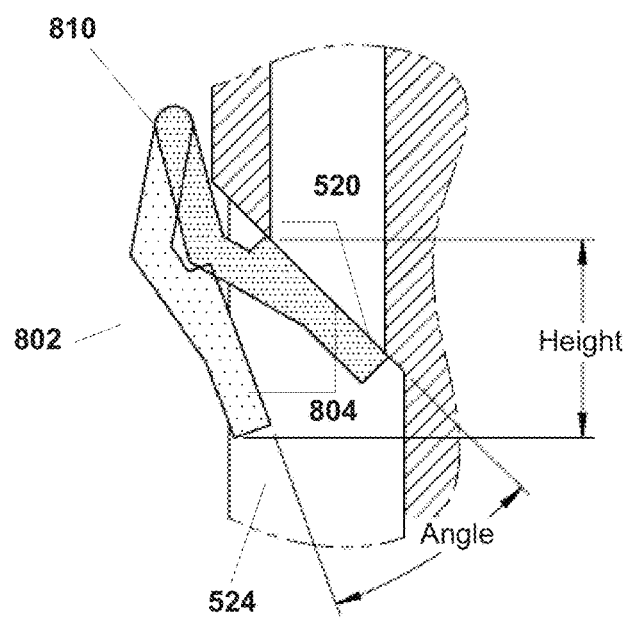
Figure 9C:
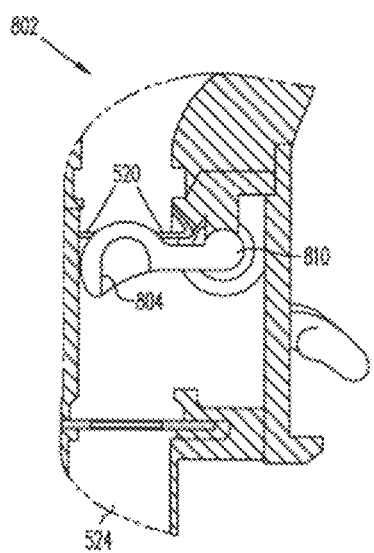
FIGS. 9C and 9D illustrate the embodiments of FIGS. 9A and 9B with the doors in the closed position.
Figure 9D:
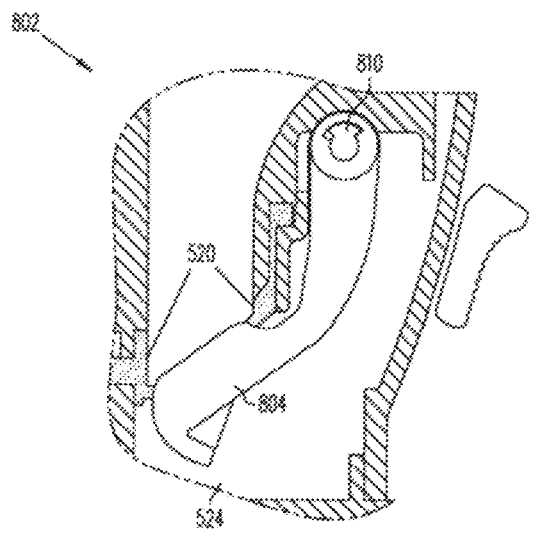

FIGS. 9A and 9B illustrate the relationship between seal angle and opening angle of a door mechanism 802 according to some embodiments of the present invention. FIG. 9A illustrates an embodiment of door mechanism 802 where seal 520 is perpendicular with respect to channel 524, for example, a seal 520 similar to that shown in FIGS. 7H and 7I. FIG. 9C illustrates an embodiment of door mechanism 802 as shown in FIG. 9A with door mechanism 802 closed. As illustrated in FIG. 9A, for a typical sized instrument channel 524, the opening angle of door mechanism 802 can be very large when an instrument such as surgical instrument 516 is inserted. In some cases, the opening angle can be 60-90°. Such a large angle results in a particularly large vertical throw (height) of sealing surface 804 and results in a large space needed to accommodate door 802 in lower part 504 above channel 524. FIG. 9B illustrates embodiments in which seal 520 has angled openings 712 with respect to channel 524. FIG. 9D illustrates an embodiment of door mechanism 802 as shown in FIG. 9B with door mechanism 802 in a closed position. In this particular example, the opening angle of door mechanism 802 can be very much smaller, in some cases as low as 20-25°. A smaller angle results in a smaller throw (height) of sealing surface 804, which can be accommodated in a much smaller space in lower part 504 above channel 524. Embodiments of door mechanism 802 according to the present invention can accommodate any seal angle. The height illustrated in FIG. 9A corresponds with an additional length of an instrument 516. The shorter height of the embodiment of FIG. 9B allow for a reduced length of an instrument 516. Also, with the small angle a smaller spring deflection at pivot 810 can be realized.

Figure 10A:
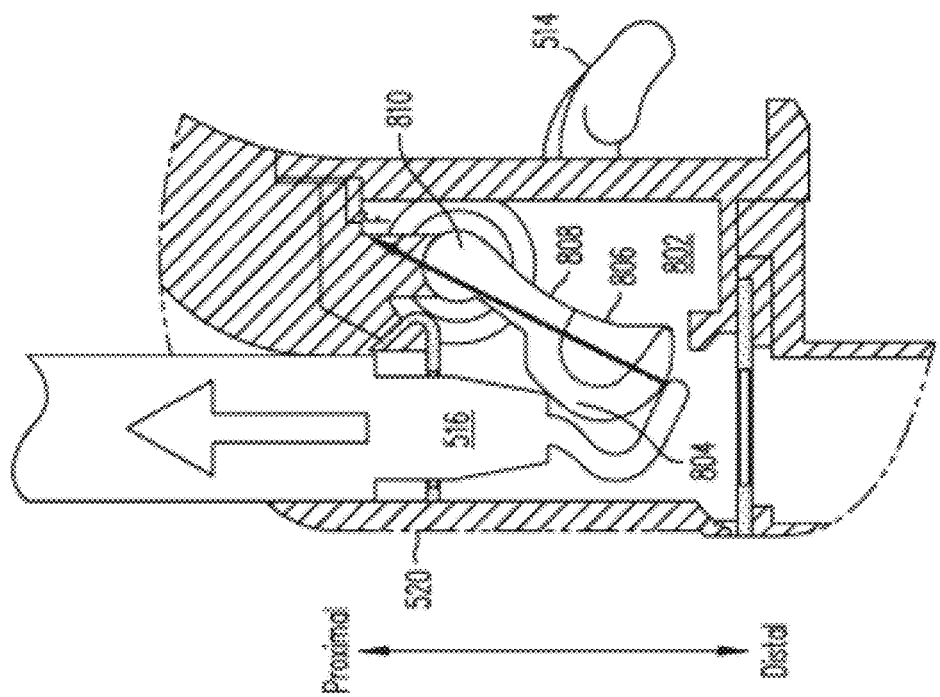
FIGS. 10A and 10B illustrate the interaction of a surgical instrument with the door mechanisms illustrated in FIGS. 9C and 9D, respectively.

In some situations, the relationship between the configuration of the door and the configuration of an instrument end effector is considered. FIG. 10A illustrates a door mechanism 802 as shown in FIG. 9C that seals with sealing surface 804 against a flat seal 520 similar to that shown in FIGS. 7J and 7K. As shown in FIG. 10A, an instrument 516 illustrated as a cautery hook instrument is being removed through seal 802 If the cautery hook end effector engages against the door, however, body 806, arm 808, and pivot 810 of door mechanism 802 are arranged in a fashion that allows the normal force F from the hook to provide a force that tends to close door mechanism 802, instead of to open door mechanism 802.

Figure 10B:
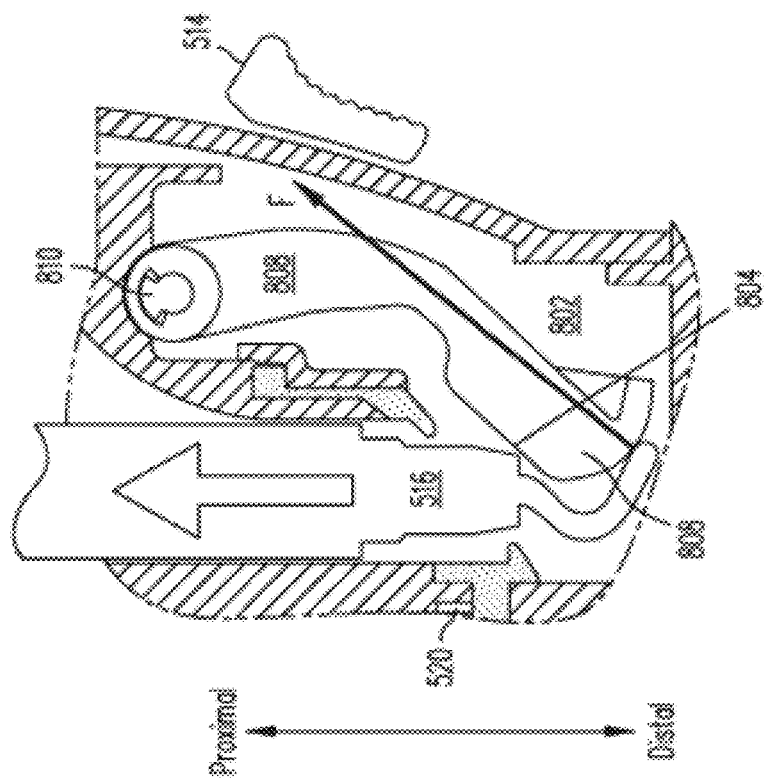

FIG. 10B illustrates embodiments of door mechanism 802 as shown in FIG. 9D, which is one of doors 510 and 512. As shown in FIG. 10B, instrument 516 is a cautery hook instrument being removed through seal 520. As shown in FIG. 10B, door mechanism 802 includes a sealing part 804 that engages with seal 520, a body part 806 that forms sealing part 804, a pivot part 810, and an arm 808 that connects pivot part 810 with body part 806, as described above. In door mechanism 802 illustrated in FIG. 10B, the angled sealing surface 804 reduces the arc through which door 802 swings in order to open and close. The shorter arc in addition to a rounded backside of door mechanism 802 allows the door to be easily pushed out of the way during instrument withdrawal and not get caught on instruments such as a cautery hook that is being removed from the instrument guide 204. The shorter arc also means the torsion springs located at pivot portion 810 go through less deflection, and so the spring force is more constant. As is illustrated in FIG. 10B, the normal force F from the hook of instrument 516 is in a direction to push door mechanism 802 open (although frictional forces may still try to pull door closed and thereby snag instruments such as a cautery hook).

The above detailed description is provided to illustrate specific embodiments of the present invention and is not intended to be limiting. Numerous variations and modifications within the scope of the present invention are possible. The present invention is set forth in the following claims.

What is claimed is:

1. A cross-slit seal, comprising:
a plurality of folded sidewalls including side surfaces extending to distal end surfaces, the distal end surfaces together forming a concave end surface when the cross-slit seal is in a closed position; and
a first slit and a second slit that intersects the first slit to form a cross-slit in the concave end surface formed by the plurality of folded sidewalls when the cross-slit seal is in a closed position.

2. The cross-slit seal of claim 1, further comprising a perimeter sidewall that is tapered in towards the concave end surface.

3. The cross-slit seal of claim 1, wherein each folded sidewall of the plurality of folded sidewalls is a continuously curved concave sidewall sized and shaped to align surgical insufflation gas pressure forces across the first slit and the second slit when the cross-slit seal is in the closed position.

4. The cross-slit seal of claim 1, wherein the first slit has a slit height and a slit width, and a ratio of slit height to slit width is less than 1:1.

5. The cross-slit seal of claim 1, wherein the first slit has a slit height and a slit width, and a ratio of slit height to slit width is about 1:2.

6. The cross-slit seal of claim 1, wherein a height of the plurality of folded sidewalls is greater than a length of the first slit.

7. The cross-slit seal of claim 1, wherein a height of the plurality of folded sidewalls is less than a length of the first slit.

8. The cross-slit seal of claim 1, further including a flange that engages a cap.

9. The cross-slit seal of claim 1, further including an inner diaphragm seal configured to engage an instrument guide.

10. The cross-slit seal of claim 1, further including an outer seal that is sized and shaped to engage an inside wall of a cannula.

11. The cross-slit seal of claim 1, further including a rib at an end surface that adjoins two of the plurality of folded sidewalls, wherein the rib is sized, shaped, and positioned to engage an inside wall of a cannula.

12. The cross-slit seal of claim 11, further comprising a second rib at a second end surface that adjoins a second two of the plurality of folded sidewalls, the second rib being sized, shaped, and positioned to engage the inside wall of the cannula, wherein the rib is at one end of the first slit and the second rib is at an opposite end of the first slit, and the ribs are sized, shaped to provide structural support to bias the second slit closed when engaged with the inside wall of the cannula.

13. A cross-slit seal, comprising:
a plurality of folded sidewalls;
first and second slits that are formed by the plurality of folded sidewalls when the cross-slit seal is in a closed position, the first and second slits forming a cross-slit; and
at least one of:
a concave end surface formed by distal end surfaces of the plurality of folded sidewalls when the cross-slit seal is in a closed position, each of plurality of folded sidewalls including side surfaces that extend to the one of the distal end surfaces, wherein the slits are in the concave end surface, and
a rib at an end surface that adjoins two of the plurality of folded sidewalls, the rib being sized, shaped, and positioned to engage an inside wall of a cannula.

14. The cross-slit seal of claim 13, wherein each folded sidewall of the plurality of folded sidewalls is a continuously curved concave sidewall sized and shaped to align surgical insufflation gas pressure forces acting across the first slit and second slits when the cross-slit seal is in the closed position.

15. The cross-slit seal of claim 13, wherein a height of the plurality of folded sidewalls is greater than a length of the first and second slits.

16. The cross-slit seal of claim 13, wherein a height of the plurality of folded sidewalls is less than a length of the first and second slits.

17. The cross-slit seal of claim 13, further comprising a second rib at a second end surface that adjoins a second two of the plurality of folded sidewalls, the second rib being sized, shaped, and positioned to engage the inside wall of the cannula, wherein the rib is at one end of the first slit and the second rib is at an opposite end of the first slit, and wherein the ribs provide structural support to bias the second slit closed when engaged with the inside wall of the cannula.

18. The cross-slit seal of claim 13, wherein the first and second slits have a slit height and a slit width, and a ratio of slit height to slit width is about 1:2.

19. A cross-slit seal comprising:
a first pair of opposing folded sidewalls that come together to define a first concave distal end surface when the cross-slit seal is in a closed position, the first pair of folded sidewalls forming a first slit in the first concave distal end surface; and
a second pair of opposing folded sidewalls that come together to define a second concave distal end surface when the cross-slit seal is in a closed position, the second pair of folded sidewalls forming a second slit in the second concave distal end surface;
wherein the second slit intersects the first slit.

20. The cross-slit seal of claim 19:
wherein each folded sidewall of the first and second pairs of folded sidewalls has a concave outer surface.

21. The cross-slit seal of claim 19 further comprising:
a perimeter sidewall that extends around a perimeter of the cross-slit seal;
wherein a first folded sidewall of the first pair of folded sidewalls comprises an outer surface;
wherein a first folded sidewall of the second pair of folded sidewalls comprises an outer surface;
wherein the outer surface of the first folded sidewall of the first pair of folded sidewalls is concave and is bounded at an edge formed with the perimeter sidewall, an edge formed with the outer surface of the first folded sidewall of the second pair of folded sidewalls, and an edge formed with the first concave distal surface; and
wherein the outer surface of the first folded sidewall of the second pair of folded sidewalls is concave and is bounded at an edge formed with the perimeter sidewall, an edge formed with the outer surface of the first folded sidewall of the first pair of folded sidewalls, and an edge formed with the second concave distal surface.

22. A cross-slit seal comprising:
a plurality of folded sidewalls that come together to form a cross-shaped and concave distal end surface;
wherein a cross-slit is formed in the distal end surface when the seal is in a closed position.

23. The cross-slit seal of claim 22:
wherein each folded sidewall of the plurality of folded sidewalls is concave.

* * * * *